(12) United States Patent
Kiss et al.

(10) Patent No.: US 9,040,699 B2
(45) Date of Patent: May 26, 2015

(54) METHOD FOR PREPARING CYCLOPROPANE DERIVATIVES

(75) Inventors: Eleonora Kiss, Brussels (BE); Erwin Blomsma, Linden (BE); Serge De Bruijn, Weert (NL); E. J. N. Remy Litjens, Heeze (NL)

(73) Assignee: Aratana Therapeutics NV, Heverlee (BE)

( * ) Notice: Subject to any disclaimer, the term of this patent is extended or adjusted under 35 U.S.C. 154(b) by 0 days.

(21) Appl. No.: 14/349,648

(22) PCT Filed: Nov. 10, 2011

(86) PCT No.: PCT/EP2011/069826
§ 371 (c)(1),
(2), (4) Date: Apr. 3, 2014

(87) PCT Pub. No.: WO2013/068042
PCT Pub. Date: May 16, 2013

(65) Prior Publication Data
US 2015/0051394 A1    Feb. 19, 2015

(51) Int. Cl.
*C07D 313/06* (2006.01)
*C07D 239/34* (2006.01)
*C07D 239/42* (2006.01)
*C07D 473/18* (2006.01)
*C07D 473/40* (2006.01)

(52) U.S. Cl.
CPC ............ *C07D 473/18* (2013.01); *C07D 473/40* (2013.01)

(58) Field of Classification Search
CPC ... C07D 239/34; C07D 329/42; C07D 313/06
USPC .......................................... 549/350; 544/320
See application file for complete search history.

(56) References Cited

FOREIGN PATENT DOCUMENTS

EP    0502690 A2    9/1992
EP    0675123 A1    10/1995

OTHER PUBLICATIONS

Chen et al., "An Improved Synthesis of 9-[2-(Diethoxyphosphonomethoxy)Ethyl]Adenine and its Analogues with Other Purine Bases Utilizing the Mitsunobu Reaction," *Nucleosides & Nucleotides*, vol. 15(11&12), pp. 1771-1778 (1996).
Onishi et al., "Synthesis and Antiviral Activity of Novel Anti-VZV 5-Substituted Uracil Nucleosides with a Cyclopropane Sugar Moiety," *J. Med. Chem.*, vol. 43, pp. 278-282 (2000).
Park et al., "Synthesis of enantiomerically pure D- and L-bicyclo[3.1.0]hexenyl carbanucleosides and their antiviral evaluation," *Bioorganic & Medicinal Chemistry*, vol. 19, pp. 3945-3955 (2011).
Sekiyama et al., "Synthesis and Antiviral Activity of Novel Acyclic Nucleosides: Discovery of a Cyclopropyl Nucleoside with Potent Inhibitory Activity against Herpesviruses," *J. Med. Chem.*, vol. 41, pp. 1284-1298 (1998).

*Primary Examiner* — Bruck Kifle
(74) *Attorney, Agent, or Firm* — Knobbe Martens Olson & Bear LLP

(57) ABSTRACT

The present invention relates to the preparation of cyclopropane derivatives, in particular 2-amino-9-[[(1S,2R)-1,2-bis(hydroxymethyl)cyclopropyl]methyl]-4,8-dihydro-1H-purin-6-one, especially via the [(1S,7R)-4-phenyl-3,5-dioxabicyclo[5.1.0]octan-1-yl]methanol intermediate.

16 Claims, No Drawings

METHOD FOR PREPARING CYCLOPROPANE DERIVATIVES

CROSS-REFERENCE TO RELATED APPLICATIONS

This application is the U.S. National Phase under 35 U.S.C. §371 of International Application PCT/EP2011/069826, filed Nov. 10, 2011.

FIELD OF THE INVENTION

The present invention relates to the preparation of cyclopropane derivatives, and to intermediates obtained in said preparation.

BACKGROUND OF THE INVENTION

Cyclopropane derivatives such as 2-amino-9-[[(1S,2R)-1,2-bis(hydroxymethyl)cyclopropyl]methyl]-1,9-dihydro-6H-purin-6-one are known to have a potent antiviral activity.

A first method for the preparation of 2-amino-9-[[(1S,2R)-1,2-bis(hydroxymethyl)cyclopropyl]methyl]-1,9-dihydro-6H-purin-6-one is disclosed in patent EP0502690. The reaction sequence disclosed in these documents involves the preparation of ethyl (1S,5R)-2-oxo-3-oxabicyclo[3.1.0]hexane-1-carboxylate from R-(−)-epichlorohydrin and diethyl malonate with high optical purity. Subsequent transformation to (1S,2R)-1,2-bis(benzoyloxymethyl)cyclopropylmethyl p-toluenesulfonate requires 8 further steps, including several protection and deprotection steps. The (1S,2R)-1,2-bis(benzoyloxymethyl)cyclopropylmethyl p-toluenesulfonate is then coupled with 2-amino-6-benzyloxy-purine. Finally, removal of all hydroxyl protecting groups results in the formation of the desired product. In one of the steps, a dimethyl ketal function is used as diol protecting group while transforming the ester function to hydroxyl. However, due to its low stability, this protecting group has to be replaced for further transformation of the hydroxyl to a leaving group.

In the synthesis of 2-amino-9-[[(1S,2R)-1,2-bis(hydroxymethyl)cyclopropyl]methyl]-1,9-dihydro-6H-purin-6-one analogues described in patent EP0649840, it is further demonstrated that the use of the more robust diphenyl ketal function eliminates the need of the replacement of the diol protecting group during the synthesis. However, setting up that protecting group requires the use of highly toxic 2,3-dichloro-5,6-dicyanobenzoquinone (DDQ) and the potentially explosive diphenyldiazomethane.

Another method for the preparation of 2-amino-9-[[(1S,2R)-1,2-bis(hydroxymethyl)cyclopropyl]methyl]-1,9-dihydro-6H-purin-6-one is disclosed in patent EP0675123. The reaction sequence disclosed in these documents is similar to the method described hereinabove. Specifically, ethyl (1S,5R)-2-oxo-3-oxabicyclo[3.1.0]hexane-1-carboxylate is prepared from R-(−)-epichlorohydrin and diethyl malonate with high optical purity. The ester function is then selectively reduced to hydroxyl, while the lactone moiety is opened and reclosed. Then, the hydroxyl group is transformed further to a leaving group and the compound is coupled with 2-amino-6-chloropurine. Finally, hydrolysis of the base moiety into guanine and subsequent reduction of the lactone ring to diol results in the formation of the desired product.

The formal synthesis of 2-amino-9-[[(1S,2R)-1,2-bis(hydroxymethyl)cyclopropyl]methyl]-1,9-dihydro-6H-purin-6-one, involving the intramolecular cyclopropanation of a D-ribose derived unsaturated diazo compound as key step, is described by Gallos et al. in Tetr. Lett. 2001, 42, 7489.

The above described methods suffer from certain disadvantages: the synthesis routes involve several time-consuming protection and deprotection steps, require the use of hazardous products, and/or involve the use of intermediates with low stability. Accordingly, there is a need for synthesis methods for cyclopropane derivatives such as 2-amino-9-[[(1S,2R)-1,2-bis(hydroxymethyl)cyclopropyl]methyl]-1,9-dihydro-6H-purin-6-one, which mitigate at least one of the problems stated above.

SUMMARY OF THE INVENTION

The object of the present invention is to provide a new and improved method for the production of 2-amino-9-[[(1S,2R)-1,2-bis(hydroxymethyl)cyclopropyl]methyl]-1,9-dihydro-6H-purin-6-one and related compounds. A further object of the invention is to provide a method which employs readily available starting materials and uses reaction conditions which are readily achievable on an industrial scale. A further object of the invention is to provide new and useful intermediates, particularly (4-phenyl-3,5-dioxabicyclo[5.1.0]octan-1-yl)methanol and/or (4-phenyl-3,5-dioxabicyclo[5.1.0]octan-1-yl)methanamine derivatives, which are represented by compound of formula (5), or a tautomer, racemate or stereoisomer thereof,

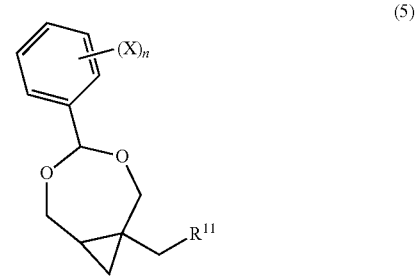

(5)

wherein n is an integer from 0 to 5 and X is selected from $C_{1-6}$alkyl, $C_{1-6}$haloalkyl, $C_{2-6}$alkenyl, $C_{2-6}$alkynyl, halogen, hydroxyl, $C_{1-6}$alkoxy or amino; and $R^{11}$ is hydroxyl or amino.

The inventors have found that by using a phenylacetal function as a diol protecting group, there is no need for replacing the diol protecting group during the synthesis of, for example, 2-amino-9-[[(1S,2R)-1,2-bis(hydroxymethyl)cyclopropyl]methyl]-1,9-dihydro-6H-purin-6-one. Furthermore, the inventors have found that setting up that protecting group proved to be a stereoselective process where the major stereoisomer could be readily isolated by crystallization. Indeed, [(1S,7R)-4-phenyl-3,5-dioxabicyclo[5.1.0]octan-1-yl]methanol and derivatives thereof proved to be very useful synthetic intermediates that could be easily isolated and stored due to its highly crystalline property.

Importantly, compounds of formula (5) can be used as a precursor in the synthesis of several 2-amino-9-[[(1S,2R)-1,2-bis(hydroxymethyl)cyclopropyl]methyl]-1,9-dihydro-6H-purin-6-one analogs. For example, compounds of formula (5a') or (5b') can be used as a precursor in the synthesis of several 2-amino-9-[[(1S,2R)-1,2-bis(hydroxymethyl)cyclopropyl]methyl]-1,9-dihydro-6H-purin-6-one analogs of formula (A'):

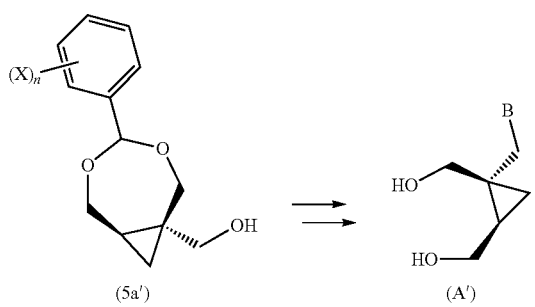

(5a′) → (A′)

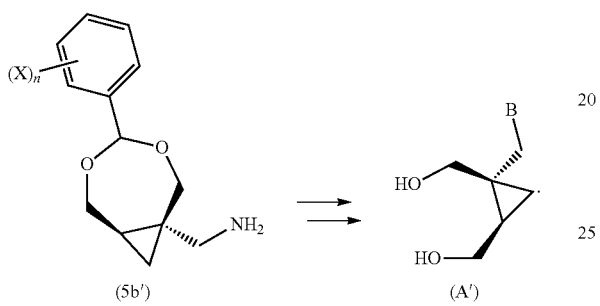

(5b′) → (A′)

wherein B is selected from the group consisting of purinyl, pyrimidyl, or aza or deaza analog thereof, or —NR$^1$R$^2$; each group being optionally substituted by one or more substituents independently selected from halo, amino, hydroxyl, C$_{1-6}$alkyl, aminoC$_{1-6}$alkyl, nitro, formamido, —NHR$^{18}$, or OR$^7$; and wherein a carbon atom of said purinyl or pyrimidyl can be oxidized to form a C═O, wherein R$^7$ is selected from C$_{1-4}$alkyl, C$_{6-10}$arylC$_{1-6}$alkylene or C$_{8-10}$aryl, R$^{18}$ is selected from C$_{6-10}$arylC$_{1-6}$alkylene, C$_{1-6}$alkylcarbonyl, haloC$_{1-6}$alkylcarbonyl, C$_{1-6}$alkyloxycarbonyl, 9-fluorenylmethyloxycarbonyl, or C$_{6-10}$arylC$_{1-6}$alkyloxycarbonyl; and R$^1$ is selected from hydrogen, C$_{6-10}$aryl, C$_{6-10}$arylC$_{1-6}$alkylene, C$_{1-4}$alkyl, C$_{6-10}$haloaryl, C$_{1-4}$haloalkyl or C$_{6-10}$haloarylC$_{1-6}$alkylene;

R$^2$ is selected from C$_{6-10}$aryl, C$_{6-10}$arylC$_{1-6}$alkylene, C$_{1-4}$alkyl, C$_{8-10}$haloaryl, C$_{1-4}$haloalkyl or C$_{6-10}$haloarylC$_{1-6}$alkylene.

Additionally, compounds of formula (5a″) or (5b″) can be used in the synthesis of several other 2-amino-9-[[(1S,2R)-1,2-bis(hydroxymethyl)cyclopropyl]methyl]-1,9-dihydro-6H-purin-6-one analogs of formula (A″):

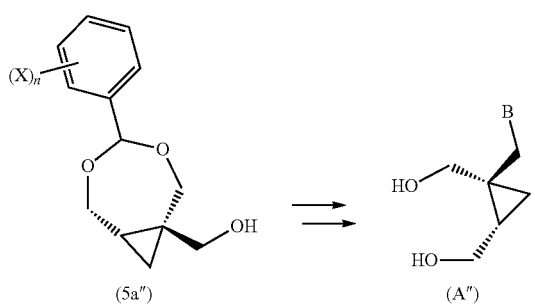

(5a″) → (A″)

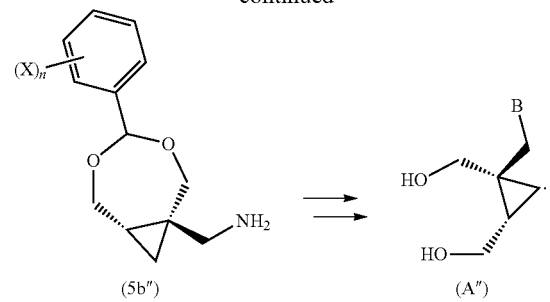

(5b″) → (A″)

Accordingly, in a first aspect, the present invention provides a compound of the formula (5) as described hereinabove, or a tautomer, racemate or stereoisomer thereof.

In a further aspect, the present invention provides a method for the preparation of a compound of formula (5) or a tautomer, racemate or stereoisomer thereof, (5)

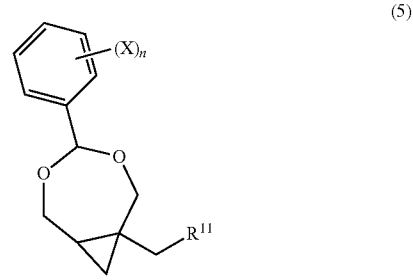

wherein n, X and R$^{11}$ have the same meaning as that defined herein, comprising the step of transforming the —COR$^{12}$ moiety of a compound of formula (4);

(4)

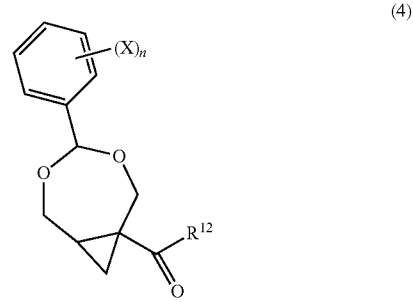

wherein R$^{12}$ is —OR$^3$ or amino and R$^3$ is selected from C$_{1-6}$alkyl, C$_{6-10}$aryl, C$_{6-10}$arylC$_{1-6}$alkylene, C$_{6-10}$haloaryl, C$_{1-6}$haloalkyl or C$_{6-10}$haloarylC$_{1-6}$alkylene.

In a further aspect, the present invention provides the use of the cyclopropane derivative of formula (5) for the preparation of a cyclopropane derivative of formula (A)

(A)

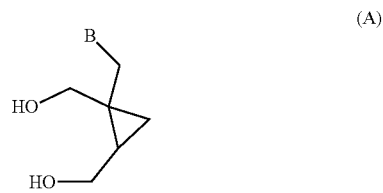

wherein B is selected from the group consisting of purinyl, pyrimidyl, or aza or deaza analog thereof, or —NR$^1$R$^2$; each group being optionally substituted by one or more substituents independently selected from halo, amino, hydroxyl, C$_{1-6}$alkyl, aminoC$_{1-6}$alkyl, nitro, formamido, —NHR$^{18}$, or OR$^7$; and wherein a carbon atom of said purinyl or pyrimidyl can be oxidized to form a C=O, wherein R$^7$ is selected from C$_{1-4}$alkyl, C$_{6-10}$arylC$_{1-6}$alkylene or C$_{6-10}$aryl, R$^{18}$ is selected from C$_{6-10}$arylC$_{1-6}$alkylene, C$_{1-6}$alkylcarbonyl, haloC$_{1-6}$alkylcarbonyl, C$_{1-6}$alkyloxycarbonyl, 9-fluorenylmethyloxycarbonyl, or C$_{6-10}$arylC$_{1-6}$alkyloxycarbonyl; and R$^1$ is selected from hydrogen, C$_{6-10}$aryl, C$_{6-10}$arylC$_{1-6}$alkylene, C$_{1-4}$alkyl, C$_{6-10}$haloaryl, C$_{1-4}$haloalkyl or C$_{6-10}$haloarylC$_{1-6}$alkylene; and R$^2$ is selected from C$_{6-10}$aryl, C$_{6-10}$arylC$_{1-6}$alkylene, C$_{1-4}$alkyl, C$_{6-10}$haloaryl, C$_{1-4}$haloalkyl or C$_{6-10}$haloarylC$_{1-6}$alkylene.

The present invention also encompasses methods for the preparation of a compound of formula (A).

DETAILED DESCRIPTION OF THE INVENTION

The present invention will be described with respect to particular embodiments but the invention is not limited thereto but only by the claims. Any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

Unless expressly stated otherwise, each of the following terms has the indicated meaning:

The term "acyl" refers to a radical formed by removal of the hydroxy from a carboxylic acid (i.e., R—C(=O)—). Preferred acyl groups include acetyl, formyl, and propionyl, with acetyl being most preferred.

The term "carbonyl" by itself or as part of another substituent, refers to the group —C(=O)—.

The term "C$_{1-6}$alkyl", as a group or part of a group, refers to a hydrocarbyl radical of Formula C$_n$H$_{2n+1}$ wherein n is a number ranging from 1 to 6. Generally, the alkyl groups comprise from 1 to 6 carbon atoms, for example 1 to 4 carbon atoms. Alkyl groups may be linear, or branched and may be substituted as indicated herein. When a subscript is used herein following a carbon atom, the subscript refers to the number of carbon atoms that the named group may contain. Thus, for example, C$_{1-4}$alkyl means an alkyl of 1 to 4 carbon atoms. Examples of alkyl groups are methyl, ethyl, propyl, isopropyl, butyl, isobutyl, sec-butyl, tert-butyl, pentyl and its chain isomers, hexyl and its chain isomers.

The term "C$_{2-6}$alkenyl" by itself or as part of another substituent, refers to an unsaturated hydrocarbyl group, which may be linear, or branched, comprising one or more carbon-carbon double bonds. Preferred alkenyl groups thus comprise between 2 and 6 carbon atoms, preferably between 2 and 4 carbon atoms. Non-limiting examples of C$_{2-6}$alkenyl groups include ethenyl, 2-propenyl, 2-butenyl, 3-butenyl, 2-pentenyl and its chain isomers, 2-hexenyl and its chain isomers, 2,4-pentadienyl and the like.

The term "C$_{2-6}$alkynyl" by itself or as part of another substituent, refers to an unsaturated hydrocarbyl group, which may be linear, or branched, comprising one or more carbon-carbon triple bonds. Preferred alkynyl groups thus comprise between 2 and 6 carbon atoms, preferably between 2 and 4 carbon atoms. Non limiting examples of C$_{2-6}$alkynyl groups include ethynyl, 2-propynyl, 2-butynyl, 3-butynyl, 2-pentynyl and its chain isomers, 2-hexynyl and its chain isomers and the like.

As used herein, the term "C$_{3-8}$cycloalkyl", by itself or as part of another substituent, refers to a saturated or partially saturated cyclic alkyl radical containing from about 3 to about 8 carbon atoms. Examples of C$_{3-8}$cycloalkyl include cyclopropyl, cyclobutyl, cyclopentyl, or cyclohexyl, cycloheptyl and cyclooctyl.

As used herein, the term "C$_{6-10}$aryl", by itself or as part of another substituent, refers to a polyunsaturated, aromatic hydrocarbyl group having a single ring (i.e. phenyl) or multiple aromatic rings fused together (e.g. naphthalene), or linked covalently, typically containing 6 to 10 atoms; wherein at least one ring is aromatic. Aryl rings may be unsubstituted or substituted with from 1 to 4 substituents on the ring. Aryl may be substituted with halo, cyano, nitro, hydroxy, carboxy, amino, acylamino, alkyl, heteroalkyl, haloalkyl, phenyl, aryloxy, alkoxy, heteroalkyloxy, carbamyl, haloalkyl, methylenedioxy, heteroaryloxy, or any combination thereof. Examples of C$_{6-10}$aryl include phenyl, naphthyl, indanyl, or 1,2,3,4-tetrahydro-naphthyl.

When the term "alkyl" is used as a suffix following another term, as in "hydroxyalkyl," this is intended to refer to an alkyl group, as defined above, being substituted with one or two (preferably one) substituent(s) selected from the other, specifically-named group, also as defined herein. The term "hydroxyalkyl" therefore refers to a —R$^a$—OH group wherein R$^a$ is alkylene as defined herein. The term "C$_{1-6}$alkoxy" or "C$_{1-6}$alkyloxy" as used herein refers to a radical having the Formula —OR$^d$ wherein R$^d$ is C$_{1-6}$alkyl. Non-limiting examples of suitable alkoxy include methoxy, ethoxy, propoxy, isopropoxy, butoxy, isobutoxy, sec-butoxy, tert-butoxy, pentyloxy and hexyloxy.

As used herein, the term "C$_{1-6}$alkylene", by itself or as part of another substituent, refers to C$_{1-6}$alkyl groups that are divalent, i.e., with two single bonds for attachment to two other groups.

Alkylene groups may be linear or branched and may be substituted as indicated herein. Non-limiting examples of alkylene groups include methylene (—CH$_2$—), ethylene (—CH$_2$—CH$_2$—), methylmethylene (—CH(CH$_3$)—), 1-methyl-ethylene (—CH(CH$_3$)—CH$_2$—), n-propylene (—CH$_2$—CH$_2$—CH$_2$—), 2-methylpropylene (—CH$_2$—CH ($CH_3$)—$CH_2$—), 3-methylpropylene (—$CH_2$—$CH_2$—CH($CH_3$)—), n-butylene (—$CH_2$—$CH_2$—$CH_2$—$CH_2$—), 2-methylbutylene (—$CH_2$—CH($CH_3$)—$CH_2$—$CH_2$—), 4-methylbutylene (—$CH_2$—$CH_2$—$CH_2$—CH($CH_3$)—), pentylene and its chain isomers, hexylene and its chain isomers.

The term "$C_{6-10}arylC_{1-6}alkylene$", as a group or part of a group, means a $C_{1-6}alkyl$ as defined herein, wherein a hydrogen atom is replaced by a $C_{6-10}aryl$ as defined herein. Examples of $C_{6-10}arylC_{1-6}alkyl$ radicals include benzyl, phenethyl, dibenzylmethyl, methylphenylmethyl, 3-(2-naphthyl)-butyl, and the like.

As used herein, the term "$C_{1-6}alkylC_{6-10}arylene$", by itself or as part of another substituent, refers to a $C_{6-10}aryl$ group as defined herein, wherein a hydrogen atom is replaced by a $C_{1-6}alkyl$ as defined herein. As used herein, the term "$C_{3-6}cycloalkylene$", by itself or as part of another substituent refers to a saturated homocyclic hydrocarbyl biradical of formula $C_nH_{2n-2}$. Non-limiting examples of cycloalkylene include 1,2-cyclopropylene, 1,1-cyclopropylene, 1,1-cyclobutylene, 1,2-cyclobutylene, 1,3-cyclopentylene, 1,1-cyclopentylene, or cyclohexylene.

The term "$aminoC_{1-6}alkyl$", by itself or as part of another substituent, refers to the group —$R_j$—$NR^kR^l$ wherein $R^j$ is $_{1-6}$ alkylene, $R^k$ is hydrogen or $C_{1-6}alkyl$ as defined herein, and $R^l$ is hydrogen or $C_{1-6}alkyl$ as defined herein.

The term "$C_{1-6}alkyl$ ether" also referred as "$C_{1-6}alkoxyC_{1-6}$ alkyl", by itself or as part of another substituent, refers to a $C_{1-6}alkyl$ group substituted with one to two $R^b$, wherein $R^b$ is $C_{1-6}alkoxy$ as defined below.

The term "$C_{2-6}alkenyl$ ether" also referred as "$C_{1-6}alkenyloxyC_{1-6}alkenyl$", by itself or as part of another substituent, refers to a $C_{1-6}alkenyl$ group substituted with one to two $R^e$, wherein $R^e$ is $C_{1-6}alkenyloxy$.

"Halo" or "halogen" is fluoro, chloro, bromo or iodo.

The term "$C_{1-6}alkylsulfinyl$", "$C_{6-10}arylsulfinyl$" or "$C_{6-10}arylC_{1-6}alkylenesulfinyl$", by itself or as part of another substituent, refers to the group —$S(O)R^x$, wherein Rx is $C_{1-6}alkyl$, $C_{6-10}aryl$ or $C_{6-10}arylC_{1-6}alkylene$, respectively. An example of $C_{1-6}alkylsulfinyl$ is methylsulfinyl.

The term "$C_{1-6}alkylsulfonyl$", "$C_{6-10}arylsulfinyl$ or $C_{6-10}arylC_{1-6}alkylenesulfonyl$, by itself or as part of another substituent, refers to the group —$S(=O)_2R^y$, wherein $R^y$ is $C_{1-6}alkyl$, $C_{6-10}aryl$ or $C_{6-10}arylC_{1-6}alkylene$, respectively. An example of $C_{1-6}alkylsulfonyl$ is methylsulfonyl.

The term "$C_{1-6}alkylthio$", "$C_{6-10}arylthio$" or "$C_{6-10}arylC_{1-6}$ alkylenethio", by itself or as part of another substituent, refers to the group —$SR^w$, wherein $R^w$ is $C_{1-6}alkyl$, $C_{6-10}aryl$ or $C_{6-10}arylC_{1-6}alkylene$, respectively. Non-limiting examples of suitable $C_{1-6}alkylthio$ include methylthio, ethylthio, propylthio, isopropyl thio, butylthio, isobutylthio, sec-butylthio, tert-butylthio, pentylthio and hexylthio.

The term "$C_{1-6}alkylsulfonate$", "$C_{6-10}arylsulfonate$ or "$haloC_{1-4}alkylsulfonate$", by itself or as part of another substituent, refers to the group —$S(=O)_2$—O—$R^v$, wherein $R^v$ is $C_{1-6}alkyl$, $C_{6-10}aryl$ or $haloC_{1-3}alkyl$, respectively. An example of $C_{1-6}alkylsulfonate$ is methylsulfonate. Examples of $haloC_{1-4}alkylsulfonate$ are nonafluorobutanesulfonate (nonaflate) and trifluoromethanesulfonate (triflate).

The term "$C_{1-6}alkylphosphonate$" or "$C_{6-10}arylphosphonate$", by itself or as part of another substituent, refers to the group —$OP(=O)(OR^t)(OR^u)$, wherein $R^t$ and $R^u$ are $C_{1-6}alkyl$ or $C_{6-10}aryl$, respectively. Preferably, $R^t$ and $R^u$ are identical. An example of $C_{1-6}alkylphosphonate$ is diethylphosphonate.

The term "formamido" as used herein refers to a —NH—C(=O)—H group.

The term "amino" by itself or as part of another substituent, refers to $NH_2$.

The term "pharmaceutically acceptable salts" or "veterinary acceptable salts" as used herein means the therapeutically active non-toxic addition salt forms which the compounds of formula are able to form and which may conveniently be obtained by treating the base form of such compounds with an appropriate base or acid. The pharmaceutically acceptable acid and base addition salts as mentioned hereinabove or hereinafter are meant to comprise the therapeutically active non-toxic acid and base addition salt forms which the compounds of Formula (A) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form. The compounds of Formula (A) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

Moreover, salts of acids or bases which are not physiologically acceptable may also find use, for example, in the preparation or purification of a physiologically acceptable compound. All salts, whether or not derived from a physiologically acceptable acid or base, are within the scope of the present invention.

The term "isomers" as used herein means all possible isomeric forms, including tautomeric forms, which the compounds of formula (A), (A'), (A"), (1) to (8) or (1') to (8') may possess. Unless otherwise stated, the standard chemical designation refers to all possible stereochemically isomeric forms, including all diastereomers and enantiomers (since the compounds described herein may have at least one chiral center) of the basic molecular structure. More particularly, unless otherwise stated, stereogenic centers may have either the R- or S-configuration, and substituents may have either cis- or trans-configuration.

Pure isomeric forms of the said compounds are defined as isomers substantially free of other enantiomeric or diastereomeric forms of the same basic molecular structure. In particular, the term "stereoisomerically pure" or "chirally pure" relates to compounds having a stereoisomeric excess of at least about 80% (i.e. at least 90% of one isomer and at most 10% of the other possible isomers), preferably at least 90%, more preferably at least 94% and most preferably at least 97%. The terms "enantiomerically pure" and "diastereomerically pure" should be understood in a similar way, having regard to the enantiomeric excess, respectively the diastereomeric excess, of the mixture in question. Consequently, if a mixture of enantiomers is obtained during any of the following preparation methods, it can be separated by liquid chromatography using a suitable chiral stationary phase. Suitable chiral stationary phases are, for example, polysaccharides, in particular cellulose or amylose derivatives. Commercially available polysaccharide based chiral stationary phases are ChiralCel™ CA, OA, OB, OC, OD, OF, OG, OJ and OK, and Chiralpak™ AD, AS, OP(+) and OT(+). Appropriate eluents or mobile phases for use in combination with said polysaccharide chiral stationary phases are hexane and the like, modified with an alcohol such as ethanol, isopropanol and the like. The terms cis and trans are used herein in accordance with Chemical Abstracts nomenclature and refer to the position of the substituents on a ring moiety. The absolute stereochemical configuration of the compounds of formula may easily be determined by those skilled in the art while using well-known methods such as, for example, X-ray diffraction.

Those of skill in the art will also recognize that the compounds of the invention may exist in many different protonation states, depending on, among other things, the pH of their environment. While the structural formulae provided herein depict the compound in only one of several possible protonation states, it will be understood that these structures are illustrative only, and that the invention is not limited to any particular protonation state, any and all protonated forms of the compounds are intended to fall within the scope of the invention.

All documents cited in the present specification are hereby incorporated by reference in their entirety.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In a first aspect, the present invention provides a compound of the formula (5):

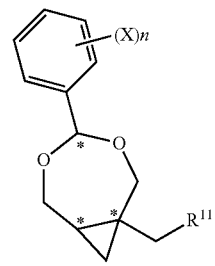

(5)

or a tautomer, racemate or stereoisomer thereof,
wherein n is an integer from 0 to 5 and X is selected from $C_{1-6}$alkyl, $C_{1-6}$haloalkyl, $C_{2-6}$alkenyl, $C_{2-6}$alkynyl, halogen, hydroxyl, $C_{1-6}$alkoxy or amino; and $R^{11}$ is hydroxyl or amino.

In particular embodiments, n is 0, 1, 2, 3, 4 or 5. In preferred embodiments, n is 0, 1 or 2, preferably 0 or 1. In some embodiments, n is 0, 1 or 2, and X is selected from $C_{1-6}$alkyl, $C_{1-6}$haloalkyl, halogen, hydroxyl, $C_{1-6}$alkoxy or amino. In certain embodiments, n is 0.

In formula (5), "*" indicates a stereogenic center. Specific stereoisomers (R or S configuration) of the compounds of formula (A) refer to resolved enantiomers of the compounds for one or more of these particular stereogenic centers. Accordingly the term "stereoisomerically pure" when used referring to compounds of formula (5), means that the compounds of formula (5) are stereochemically pure in one or more of the stereogenic centers marked with "*". If the group X contains a stereogenic center, this can be of R, S or RS stereochemistry, unless stated otherwise.

In particular embodiments, the compounds of formula (5) according to the present invention are stereoisomerically pure. In certain embodiments, the compound of formula (5) is compound of formula (5') or (5"):

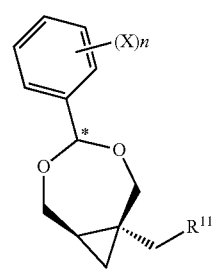

(5')

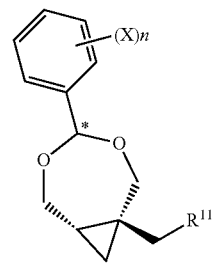

(5")

In formula (5') and (5"), "*" indicates a stereogenic center, which can be of R, S or RS stereochemistry.

In a further aspect, the present invention, also encompasses a method for the preparation of a compound of formula (5) or a tautomer, racemate or stereoisomer thereof, comprising the step of transforming the —COR$^{12}$ moiety of a compound of formula (4) thereby obtaining the compound of formula (5);

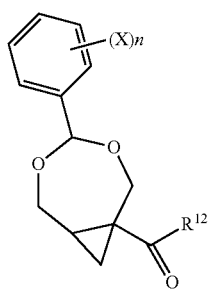

(4)

wherein R$^{12}$ is —OR$^3$ or amino and R$^3$ is selected from C$_{1-6}$alkyl, C$_{6-10}$aryl, C$_{6-10}$arylC$_{1-6}$alkylene, C$_{6-10}$haloaryl, C$_{1-6}$haloalkyl or C$_{6-10}$haloarylC$_{1-6}$alkylene.

In some embodiments, the preparation of said compound of formula (4) comprises reacting a compound of formula (2) with a compound of formula (3):

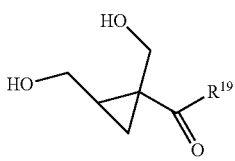

(2)

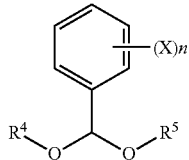

(3)

thereby obtaining a compound (4a)

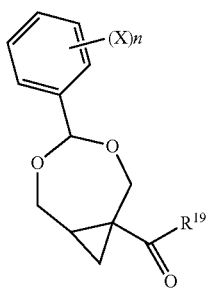

(4a)

wherein R$^{19}$ is OR$^{23}$ and R$^{23}$ is selected from C$_{1-6}$alkyl, C$_{6-10}$aryl, C$_{6-10}$arylC$_{1-6}$alkylene, C$_{6-10}$haloaryl, C$_{1-6}$haloalkyl or C$_{6-10}$haloarylC$_{1-6}$alkylene, and R$^4$ and R$^5$ are each independently selected from C$_{1-6}$alkyl, C$_{6-10}$arylC$_{1-6}$alkylene or C$_{6-10}$aryl.

In a further embodiment, the method further comprises the step of transforming the ester moiety of compound (4a) into an amide moiety, thereby obtaining a compound of formula (4b)

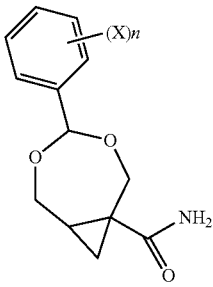

(4b)

wherein X and n have the same meaning as that defined above.

The compounds of formula (5), (5') or (5") are particularly useful as a precursor in the synthesis of compounds of formula (A), (A') or (A") as described hereinbelow.

In a further aspect, the present invention provides a method for the preparation of a compound of formula (A):

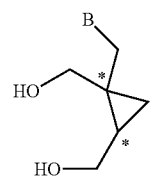

(A)

or a tautomer, a racemate, a stereoisomer, a pharmaceutically acceptable salt, a hydrate, or solvate thereof, wherein B is selected from the group consisting of purinyl, pyrimidyl, or aza or deaza analog thereof, or —NR$^1$R$^2$; each group being optionally substituted by one or more substituents independently selected from halo, amino, hydroxyl, C$_{1-6}$alkyl, aminoC$_{1-6}$alkyl, nitro, formamido, —NHR$^{18}$, or OR$^7$; and wherein a carbon atom of said purinyl or pyrimidyl can be oxidized to form a C=O, wherein R$^7$ is selected from C$_{1-4}$alkyl, C$_{6-10}$arylC$_{1-6}$alkylene or C$_{6-10}$aryl, R$^{18}$ is selected from C$_{6-10}$arylC$_{1-6}$alkylene, C$_{1-6}$alkylcarbonyl, haloC$_{1-6}$alkylcarbonyl, C$_{1-6}$alkyloxycarbonyl, 9-fluorenylmethyloxycarbonyl, or C$_{6-10}$arylC$_{1-6}$alkyloxycarbonyl; and R$^1$ is selected from hydrogen, C$_{6-10}$aryl, C$_{6-10}$arylC$_{1-6}$alkylene, C$_{1-4}$alkyl, C$_{6-10}$haloaryl, C$_{1-4}$haloalkyl or C$_{6-10}$haloarylC$_{1-6}$alkylene;

R$^2$ is selected from C$_{6-10}$aryl, C$_{6-10}$arylC$_{1-6}$alkylene, C$_{1-4}$alkyl, C$_{6-10}$haloaryl, C$_{1-4}$haloalkyl or C$_{6-10}$haloarylC$_{1-6}$alkylene.

In particular embodiments, R$^{18}$ is selected from 9-fluorenylmethyloxycarbonyl, tert-butyloxycarbonyl, benzyloxycarbonyl, methylcarbonyl, benzyl and triphenylmethyl.

In particular embodiments, B represents purinyl or a purinyl derivative preferably bound via the 9-position of the purine ring, a pyrimidyl or a pyrimidyl derivative or aza and/or deaza analogs thereof. In aza analogs, at least one carbon in B is replaced by nitrogen; in deaza analogs, at least one nitrogen in B is replaced by carbon. Combinations of such replacements are also included within the scope of the invention.

Preferred purinyl derivatives are adenyl, guanyl, 2-amino-6-chloropurinyl, 2-aminopurinyl, 2,6-diaminopurinyl, xanthyl or hypoxhanthyl. Preferred pyrimidyl derivatives are thyminyl, uracilyl and cytosinyl. Accordingly, in particular embodiments, B is selected from the group comprising purinyl, adenyl, guanyl, 2-amino-6-chloropurinyl, 2-aminopurinyl, 2,6-diaminopurinyl, xanthyl or hypoxhanthyl, pyrimidyl, thyminyl, uracilyl and cytosinyl.

In certain embodiments, B represents 2-amino-6-chloropurinyl or guanyl.

The compound of formula (A) may exist in both unsolvated and solvated forms. The term "solvate" is used herein to describe a molecular complex comprising compound (A) and a stoichiometric amount of one or more pharmaceutically acceptable solvent molecules, for example, ethanol. The term "hydrate" is employed when said solvent is water.

In formula (A), "*" indicates a stereogenic center. Specific stereoisomers (R or S configuration of a certain stereogenic center) of the compounds of formula (A) refer to resolved enantiomers of the compounds for these particular stereogenic centers. Accordingly the term "stereoisomerically pure" when used referring to compounds of formula (A), means that the compounds of Formula (A) are stereochemically pure in the stereogenic centers marked with "*". If group B contains a stereogenic center, this can be of R, S or RS stereochemistry, unless stated otherwise.

In particular embodiments, the compounds of Formula (A) according to the present invention are stereoisomerically pure. In more particular embodiments, the compound of formula (A) is a specific enantiomer of formula (A') or (A"):

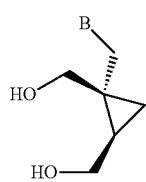

(A')

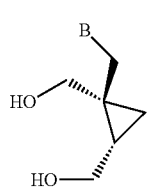

(A")

In particular embodiments, the compound of formula (A) is 2-amino-9-[[(1S,2R)-1,2-bis(hydroxymethyl)cyclopropyl]methyl]-1,9-dihydro-6H-purin-6-one, represented by formula (Ac').

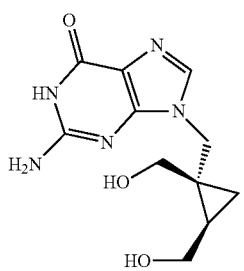

(Ac')

The present invention also encompasses a method for the preparation of a compound of formula (A),

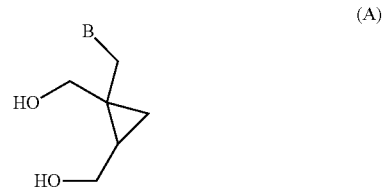

(A)

or a tautomer, a racemate, a stereoisomer, a pharmaceutically acceptable salt, a hydrate, or solvate thereof,
wherein B is selected from the group comprising purinyl, pyrimidyl, or aza or deaza analog thereof, or —NR$^1$R$^2$; each group being optionally substituted by one or more substituents independently selected from halo, amino, hydroxyl, $C_{1-6}$alkyl, amino$C_{1-6}$alkyl, nitro, formamido, —NHR$^{18}$ or OR$^7$; and wherein a carbon atom of said purinyl or pyrimidyl can be oxidized to form a C=O, wherein R$^7$ is selected from $C_{1-4}$alkyl, $C_{6-10}$aryl$C_{1-6}$alkylene or $C_{6-10}$aryl, R$^{18}$ is selected from $C_{6-10}$aryl$C_{1-6}$alkylene, $C_{1-6}$alkylcarbonyl, halo$C_{1-6}$alkylcarbonyl, $C_{1-6}$alkyloxycarbonyl, 9-fluorenylmethyloxycarbonyl, or $C_{6-10}$aryl$C_{1-6}$alkyloxycarbonyl; and
R$^1$ is selected from hydrogen, $C_{6-10}$aryl, $C_{6-10}$aryl$C_{1-6}$alkylene, $C_{1-4}$alkyl, $C_{6-10}$haloaryl, $C_{1-4}$haloalkyl or $C_{6-10}$haloaryl$C_{1-6}$alkylene;
R$^2$ is selected from $C_{6-10}$aryl, $C_{6-10}$aryl$C_{1-6}$alkylene, $C_{1-4}$alkyl, $C_{6-10}$haloaryl, $C_{1-4}$haloalkyl or $C_{6-10}$haloaryl$C_{1-6}$alkylene;
comprising the step of hydrolyzing or reducing a compound of formula (8);

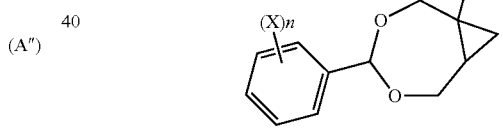

(8)

wherein n is an integer from 0 to 5 and X is $C_{1-6}$alkyl, $C_{1-6}$haloalkyl, $C_{2-6}$alkenyl, $C_{2-6}$alkynyl, halogen, hydroxyl, $C_{1-6}$alkoxy or amino; and
wherein B' is B or selected from the group consisting of purinyl, pyrimidyl, or aza or deaza analog thereof, or —NR$^1$R$^2$; each group being optionally substituted by one or more substituents independently selected from halo, amino, hydroxyl, $C_{1-6}$alkyl, amino$C_{1-6}$alkyl, nitro, formamido, —NHR$^{18}$, —NR$^{24}$R$^{25}$ or OR$^7$; and wherein a carbon atom of said purinyl or pyrimidyl can be oxidized to form a C=O, wherein R$^7$ is selected from $C_{1-4}$alkyl, $C_{6-10}$aryl$C_{1-6}$alkylene or $C_{6-10}$aryl, R$^{18}$ is selected from $C_{6-10}$aryl$C_{1-6}$alkylene, $C_{1-6}$alkylcarbonyl, halo$C_{1-6}$alkylcarbonyl, $C_{1-6}$alkyloxycarbonyl, 9-fluorenylmethyloxycarbonyl, or $C_{6-10}$aryl$C_{1-6}$alkyloxycarbonyl, R$^{24}$ and R$^{25}$ are independently hydrogen or $C_{1-6}$alkyl; and
R$^1$ is selected from hydrogen, $C_{6-10}$aryl, $C_{6-10}$aryl$C_{1-6}$alkylene, $C_{1-4}$alkyl, $C_{6-10}$haloaryl, $C_{1-4}$haloalkyl or $C_{6-10}$haloaryl$C_{1-6}$alkylene;
R$^2$ is selected from $C_{6-10}$aryl, $C_{6-10}$aryl$C_{1-6}$alkylene, $C_{1-4}$alkyl, $C_{6-10}$haloaryl, $C_{1-4}$haloalkyl or $C_{6-10}$haloaryl$C_{1-6}$alkylene.

In some embodiments, said compound of formula (8) is prepared by coupling a compound of formula (5a) with a compound of formula B'—H,

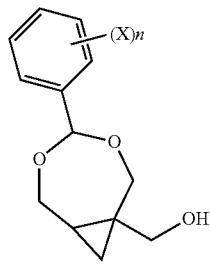
(5a)

wherein X and n have the same meaning as that defined in claim 1, B' has the same meaning as that defined herein above and H is hydrogen.

In some embodiment, prior to coupling compound of formula (5a) with compound B'—H, the hydroxyl moiety of the compound of formula (5) is transformed to obtain a compound of formula (6):

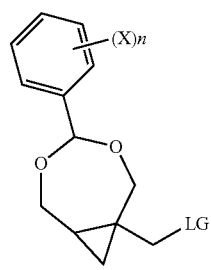
(6)

wherein LG represents a leaving group selected from halo, mesylate, tosylate, azide, nosylate, triflate, cyano or imidazolyl.

The method can also further comprises the steps of the step of reacting a compound of formula (5b) with a compound of formula (13)

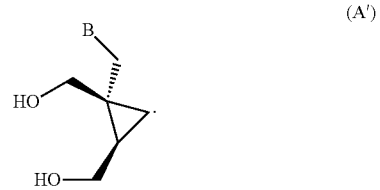
(5b)

(13)

wherein $R^{15}$ is —$OR^{27}$ or $R^{28}$, $R^{16}$ is selected from the group consisting of amino, nitro, formamido and hydrogen, $R^{17}$ is selected from halo, $C_{1-6}$alkoxy, $C_{1-6}$aryloxy, $C_{6-10}$aryl$C_{1-6}$alkyleneoxy, $C_{1-6}$alkylsulfinyl, $C_{6-10}$arylsulfinyl, $C_{6-10}$aryl$C_{1-6}$alkylenesulfinyl, $C_{1-6}$alkylsulfonyl, $C_{6-10}$arylsulfinyl, $C_{6-10}$aryl$C_{1-6}$alkylenesulfonyl, $C_{1-6}$alkylthio, $C_{6-10}$arylthio, $C_{6-10}$aryl$C_{1-6}$alkylenethio, $C_{1-6}$alkylsulfonate, $C_{6-10}$arylsulfonate, halo$C_{1-4}$alkylsulfonate, $C_{1-6}$alkylphosphonate and $C_{6-10}$arylphosphonate;

$R^{27}$ is selected from the group consisting of hydrogen, $C_{1-6}$alkyl, $C_{6-10}$aryl and $C_{6-10}$aryl$C_{1-6}$alkylene, $R^{28}$ is selected from halo, $C_{1-6}$alkoxy, $C_{1-6}$aryloxy, $C_{6-10}$aryl$C_{1-6}$alkyleneoxy, $C_{1-6}$alkylsulfinyl, $C_{6-10}$arylsulfinyl, $C_{6-10}$aryl$C_{1-6}$alkylenesulfinyl, $C_{1-6}$alkylsulfonyl, $C_{6-10}$arylsulfinyl, $C_{6-10}$aryl$C_{1-6}$alkylenesulfonyl, $C_{1-6}$alkylthio, $C_{6-10}$arylthio, $C_{6-10}$aryl$C_{1-6}$alkylenethio, $C_{1-6}$alkylsulfonate, $C_{6-10}$arylsulfonate, halo$C_{1-4}$alkylsulfonate, $C_{1-6}$alkylphosphonate and $C_{6-10}$arylphosphonate; and $R^{26}$ is selected from, hydrogen, $C_{6-10}$aryl$C_{1-6}$alkylene or $COR^{36}$, wherein $R^{30}$ is selected from $C_{1-6}$alkyl, halo$C_{1-6}$alkyl, $C_{1-6}$alkyloxy, 9-fluorenylmethyloxy, or $C_{6-10}$aryl$C_{1-6}$alkyloxy.

In some embodiments, compound (5a) or (5b) can be prepared using a method as described herein above for preparing compound of formula (5).

The method can further comprises the step of crystallizing and purifying said compound of formula (5a) or (5b).

Preferably, in the present method, the compound of formula (A) is a compound of formula (A')

(A')

In an embodiment, the method for the preparation of a compound of formula (A) can be preformed as shown in Scheme I.

SCHEME I

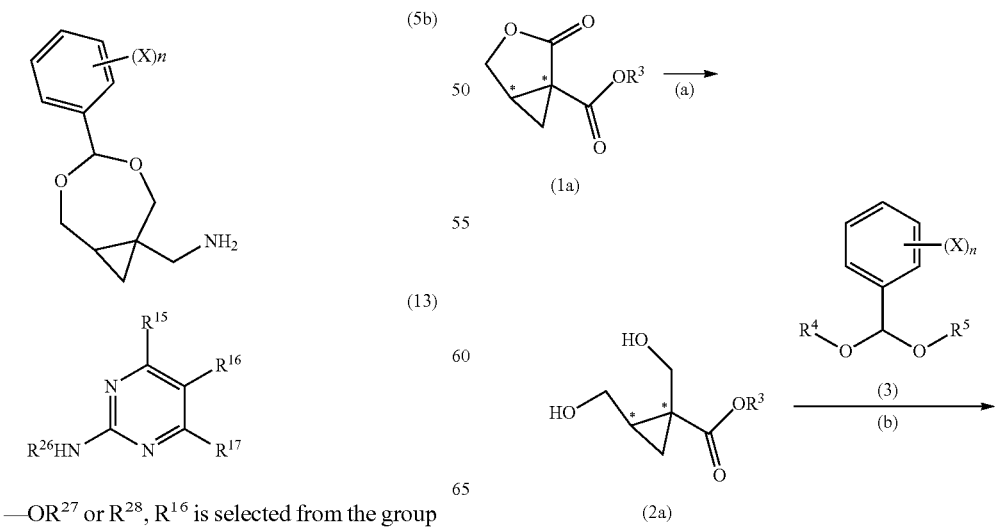

(1a)

(2a)

-continued

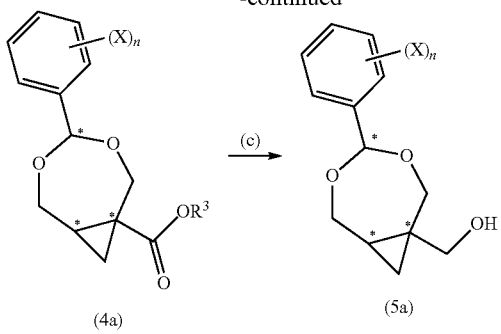

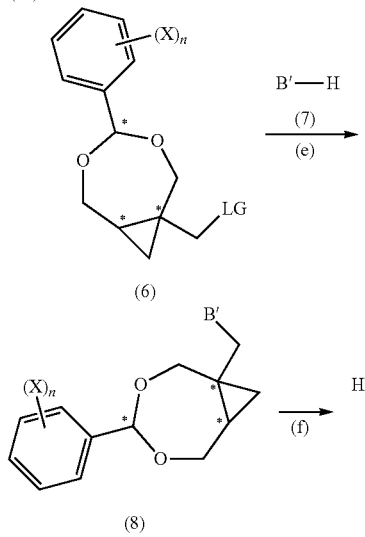

Wherein n, X and B have the same meaning as that defined above, H is hydrogen and B' is B or is selected from the group consisting of purinyl, pyrimidyl, or aza or deaza analog thereof, or —$NR^1R^2$; each group being optionally substituted by one or more substituents independently selected from halo, amino, hydroxyl, $C_{1-6}$alkyl, amino$C_{1-6}$alkyl, nitro, formamido, —$NHR^{18}$, or $OR^7$; and wherein a carbon atom of said purinyl or pyrimidyl can be oxidized to form a C=O, wherein $R^7$ is selected from $C_{1-4}$alkyl, $C_{6-10}$aryl$C_{1-6}$alkylene or $C_{6-10}$aryl, $R^{18}$ is selected from $C_{6-10}$aryl$C_{1-6}$alkylene, $C_{1-6}$alkylcarbonyl, halo$C_{1-6}$alkylcarbonyl, $C_{1-6}$alkyloxycarbonyl, 9-fluorenylmethyloxycarbonyl, or $C_{6-10}$aryl$C_{1-6}$alkyloxycarbonyl; and $R^1$ is selected from hydrogen, $C_{6-10}$aryl, $C_{6-10}$aryl$C_{1-6}$alkylene, $C_{1-4}$alkyl, $C_{6-10}$haloaryl, $C_{1-4}$haloalkyl or $C_{6-10}$haloaryl$C_{1-6}$alkylene;

$R^2$ is selected from $C_{6-10}$aryl, $C_{6-10}$aryl$C_{1-6}$alkylene, $C_{1-4}$alkyl, $C_{6-10}$haloaryl, $C_{1-4}$haloalkyl or $C_{6-10}$haloaryl$C_{1-6}$alkylene.

$R^3$ is selected from $C_{1-6}$alkyl, $C_{6-10}$aryl, $C_{6-10}$aryl$C_{1-6}$alkylene, $C_{6-10}$haloaryl, $C_{1-6}$haloalkyl or $C_{6-10}$haloaryl$C_{1-6}$alkylene.

$R^4$ and $R^5$ are each independently selected from $C_{1-6}$alkyl, $C_{6-10}$aryl$C_{1-6}$alkylene or $C_{6-10}$aryl.

In Scheme I, "*" indicates a stereogenic center. In preferred embodiments, the method according to the present invention is stereoselective in that the configuration of the stereogenic centers in the cyclopropane moiety is conserved. Scheme I' shows the preparation of specific enantiomers of the cyclopropane derivatives. However, the method of the present invention is not limited to these enantiomers, but can be used to obtain any enantiomer of formula (A), depending on the configuration of the starting products.

SCHEME I'

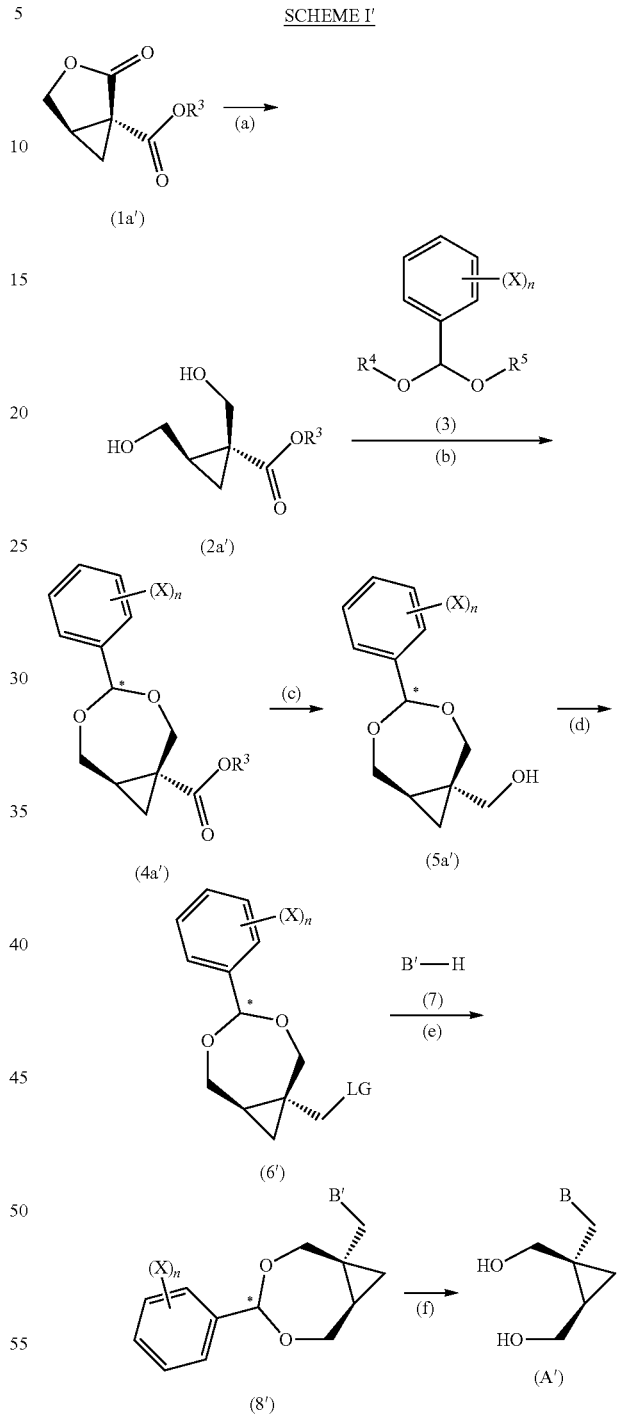

In Scheme I', "*" indicates a stereogenic center which can be of R, S or RS stereochemistry, unless stated otherwise.

In particular embodiments as illustrated in schemes I and I', the method according to the present invention starts with a lactone ester (1a) or (1a'), which can be prepared by a procedure known to the skilled in the art, preferably by the method described in *Helvetica Chimica Acta* 1989, 72(6), 1301 or in patent EP0502690. Lactone ester (1a) or (1a') can comprise a protecting group $R^3$, selected from the group comprising $C_{6-10}$aryl, $C_{6-10}$aryl$C_{1-6}$alkylene, $C_{1-6}$alkyl, $C_{6-10}$haloaryl, $C_{1-6}$haloalkyl or $C_{6-10}$haloaryl$C_{1-6}$alkylene. In particular embodiments, $R^3$ is a $C_{6-10}$aryl or $C_{1-4}$alkyl. In preferred embodiments, $R^3$ is phenyl, benzyl, methyl, ethyl, propyl, isopropyl or t-butyl. In more preferred embodiments, $R^3$ is a methyl, ethyl or phenyl group.

In preferred embodiments, the lactone ester (1a) or (1a') is selectively reduced to obtain compounds of formula (2a) or (2a'), as shown in step (a) of Scheme I and Scheme I'. The selective reduction can be obtained with one or more reducing agents, preferably in the presence of a suitable solvent. The one or more reducing agents such as metal hydride compounds, for example metal hydride compound can be selected from the group comprising $NaBH_4/CeCl_3$, $LiAlH_4$, $NaBH_4$, $NaBH(OAc)_3$, and $ZnBH_4$. Preferably, the one or more reducing agents comprise an alkaline borohydride or an alkaline aluminium hydride, more preferably sodium borohydride or lithium aluminium hydride.

Non-limiting examples of suitable solvents can be preferably ethanol or tetrahydrofuran (THF). Step (a) is optional, and may be replaced by any other method to obtain the compound of formula (2a) or (2a').

In particular embodiments, the compound of formula (2a) or (2a') can be condensed according to step (b) in Scheme I and I' with a compound of formula (3). In the compound of formula (3), $R^4$ and $R^5$ are each independently selected from $C_{1-6}$alkyl, $C_{6-10}$aryl$C_{1-6}$alkylene or $C_{6-10}$aryl. In particular embodiments, $R^4$ and $R^5$ are identical groups, preferably methyl; n is an integer from 0 to 5 and X is selected from $C_{1-6}$alkyl, $C_{1-6}$haloalkyl, $C_{2-6}$alkenyl, $C_{2-6}$alkynyl, halogen, hydroxyl, $C_{1-6}$alkoxy or amino.

In preferred embodiments, X is a $C_{1-4}$alkyl or a halogen. In particular embodiments, n is 0, 1, 2, 3, 4 or 5. Preferably, n is 0, 1 or 2, more preferably 0 or 1.

In some embodiments, compound of formula (3) can be a dialkoxymethylbenzene, including dimethoxymethylbenzene, which is either commercially available or made by procedures known to the skilled person, to obtain a compound of formula (4a) or (4a').

In particular embodiments, the condensation reaction (b) can be performed in the presence of one or more acid catalysts, optionally in a suitable solvent, such as an aprotic solvent, preferably cyclohexane and/or toluene, to obtain a compound of formula (4a) or (4a'). In preferred embodiments, the one or more acid catalysts can be selected from camphor sulfonic acid, methanesulfonic acid and/or sulfuric acid.

Step (b) in the present method has the advantages that it eliminates the need of hazardous compounds such as dichloro-5,6-dicyanobenzoquinone (DDQ) and the potentially explosive diphenyldiazomethane, as used in the method disclosed in patent EP0649840.

In particular embodiments, the ester moiety of the compound of formula (4a) or (4a') can be selectively reduced to an alcohol of formula (5a) or (5a'), as shown in step (c) of Scheme I and Scheme I'. In preferred embodiments, this is obtained using one or more reducing agents, preferably in the presence of one or more solvents, preferably ethanol and/or THF. Preferred reducing agents are sodium borohydride, lithium borohydride, lithium aluminium hydride, diisobutylaluminum hydride, lithium triethylborohydride and lithium tri-sec-butylborohydride.

The formation of a compound of formula (5a) or (5a') has the advantage that such a compound can be purified and/or isolated on a large scale by crystallization. Accordingly, in preferred embodiments, step (c) is followed by crystallizing and purifying the compound of formula (5a) or (5a'). In particular embodiments, the crystallization is performed in mixture of a polar solvent and an apolar solvent, preferably at a temperature ranging from 0° C. to 70° C. Preferred polar solvents are dichloromethane, tetrahydrofuran, ethylacetate, acetone, dimethylformamide, acetonitrile and dimethyl sulfoxide. Preferred apolar solvents are petroleum ether, pentane, cyclopentane, hexane, cyclohexane, benzene, toluene, 1,4-dioxane, chloroform and diethylether.

In a next (optional) step (d), the hydroxyl group of the compound of formula (5a) or (5a') may be transformed to a leaving group (LG), thereby obtaining the compound of formula (6) or (6'). In preferred embodiments, the leaving group is a fluoro, chloro, iodo, bromo, mesylate, tosylate, azide, nosylate, triflate, cyano or imidazolyl. In specific embodiments, the leaving group is selected from the group comprising a halogen, mesylate and tosylate. In further embodiments, the compound of formula (6) or (6') can be prepared from compounds of formula (5a) or (5a') with a halogenating reagent such as thionyl halide, acyl halide or phosphorus halide, a mesylating reagent such as methanesulfonyl halide or a tosylating reagent such as p-tolylsulfonyl halide. The reaction can be performed in the presence of a base such as triethylamine, dimethylaminopyridine and/or pyridine. The reaction can be performed in a suitable solvent, such as in an aprotic solvent (preferably THF and/or dichloromethane) without or with a catalyst such as dimethylformamide and/or dimethylaminopyridine.

In other embodiments, the leaving group is a halogen, wherein the compound of formula (6) or (6') is synthesized from compounds of formula (5a) or (5a') which are reacted with a halogenating reagent, preferably carbon tetrachloride, carbon tetrabromide or iodine, in the presence of triphenylphosphine. The reaction can be performed in the presence of a conventional solvent, preferably acetonitrile and/or dichloromethane, without or with a base such as triethylamine and/or imidazole.

In a subsequent (optional) step (e), compounds of formula (6) or (6') may be condensed with a compound B'—H (7), to obtain the compounds of formula (8) or (8'). In particular embodiments, the compound (7) is a purine or pyrimidine derivative, preferably a purine derivative (7a) as shown in Scheme IIa, or a pyrimidine derivative (7b) as shown in Scheme IIb.

SCHEME IIa

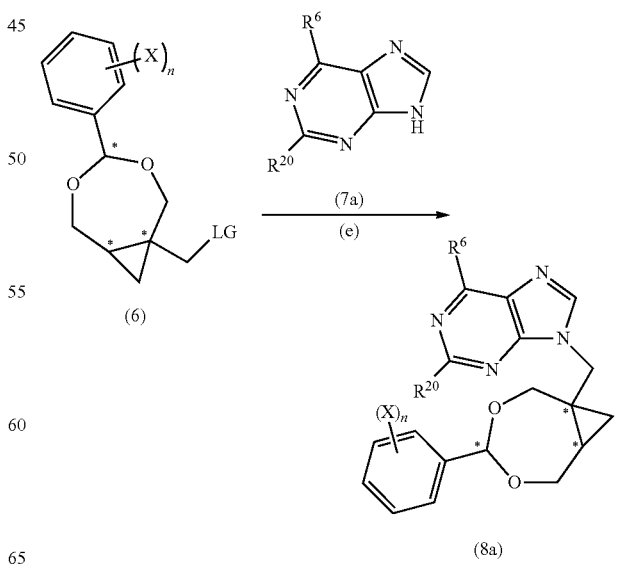

In the compound of formula (7a), which is either commercially available or made by procedures known to the skilled person, $R^6$ is selected from hydrogen, hydroxyl, $C_{1-6}$alkoxy, $C_{1-6}$thioalkyl, halogen (fluoro, chloro, iodo, bromo), $-OR^7$ or $NR^9R^9$, and $R^{29}$ is selected from $NH_2$, $NHR^{21}$, hydrogen, $NO_2$, halogen, wherein $R^{21}$ is selected from $C_{6-10}$aryl$C_{1-6}$alkylene or $COR^{22}$, $R^{22}$ is selected from $C_{1-6}$alkyl, halo$C_{1-6}$alkyl, $C_{1-6}$alkyloxy, 9-fluorenylmethyloxy, or $C_{6-10}$aryl$C_{1-6}$alkyloxy. $R^7$ is selected from $C_{1-4}$alkyl, $C_{6-10}$aryl$C_{1-6}$alkylene or $C_{6-10}$aryl. $R^8$ and $R^9$ are independently hydrogen or $C_{1-6}$alkyl. In preferred embodiments, $R^6$ is selected from chloro, bromo, $C_{1-6}$alkoxy or $C_{1-6}$thioalkyl, more preferably chloro. In particular embodiments, $R^{21}$ is selected from 9-fluroenylmethyloxycarbonyl, tert-butyloxycarbonyl, benzyloxycarbonyl, methylcarbonyl, benzyl and triphenylmethyl.

When $R^{29}$ is $NHR^{21}$, the coupling with compound (7a) can be followed by a deprotection step to afford a compound of formula (8a) wherein $R^{29}$ is $NH_2$.

When $R^{20}$ is $NO_2$ the coupling with compound of formula (7a) can be followed by a reduction step using a reducing agent selected from the group comprising Zn, Fe, Mg, FeHCl, $SnCl_2HCl$, $PdH_2$, $NiH_2$, or $Na_2S_2O_4$ to obtain a compound of formula (8a) wherein $R^{29}$ is $NH_2$.

When $R^{29}$ is halogen such as chloro, the $NH_2$ group can be introduced after the coupling with compound (7a) using for example $NH_3MeOH$. When $R^{29}$ is hydrogen, after the coupling with compound of formula (7a) a $NO_2$ group can be introduced as $R^{20}$, using for example $(n\text{-Butyl})_4N^+NO_3^-/$ trifluoracetic anhydride or $Cu(NO_3)_2$acetic anhydride. The $NO_2$ group can then be reduced into $NH_2$ using a reducing agent selected from the group comprising Zn, Fe, Mg, FeHCl, $SnCl_2HCl$, $PdH_2$, $NiH_2$, or $Na_2S_2O_4$ to obtain a compound of formula (8a) wherein $R^{29}$ is $NH_2$.

In certain embodiments, compound (7a) is adenine, guanine, 2-amino-6-chloropurine, 2-aminopurine, 2,6-diaminopurine, xanthine or hypoxhanthine. In specific embodiments, compound (7a) is 2-amino-6-chloropurine or guanine.

In certain embodiments, compound (7a) is purine, 2-nitropurine, 2-chloropurine, 2-acetylaminopurine, 2-benzylaminopurine, 2-N-tert-butylcarbamylpurine, 2-nitro-6-aminopurine, 2-nitro-6-chloropurine, 2-chloro-6-aminopurine, 2-acetylamino-6-aminopurine, 2-benzylamino-6-aminopurine, 2-N-tert-butylcarbamyl-6-chloropurine.

SCHEME IIb

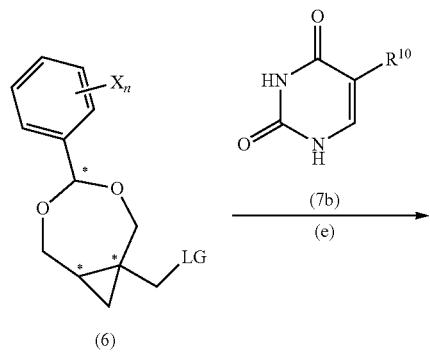

(6)

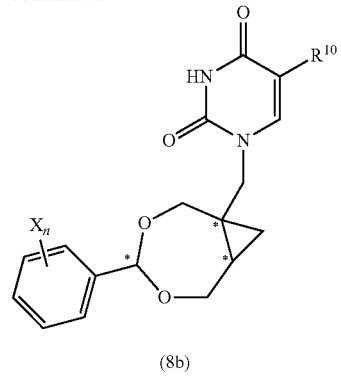

(8b)

In the compound of formula (7b), which is either commercially available or made by procedures known to the skilled person, $R^{10}$ is a halogen, a $C_{2-5}$alkyl, a trifluoromethyl, a $C_{1-6}$haloalkyl, a $C_{2-6}$alkenyl or a $C_{2-6}$alkynyl.

In particular embodiments, the compound (7b) is thymine, uracil or cytosine.

In preferred embodiments, the condensation reaction (e) is performed using a strong base, preferably sodium hydride or potassium carbonate. The reaction can be performed in a polar aprotic solvent, preferably acetonitrile or dimethylformamide and can be performed with or without a chelating agent such as preferably HMPA or 18-crown-6.

In some embodiments, step (e) is particularly advantageous when the compound (7) is a purine derivative. The inventors found that in step (e), the alkylation reaction occurs preferably at N-9, as shown in formula (8a) in Scheme IIa, which reduces or eliminates the need of a further purification step as seen in prior art.

As described hereinabove, steps (d) and (e) as shown in Scheme I and Scheme I' are optional.

In particular embodiments, the compounds of formula (5a) or (5a') are coupled with the compound (7) under Mitsunobu conditions, thereby obtaining a compound (8) or (8'), as shown in Scheme III and Scheme III'. Accordingly, step (e') as shown in Scheme III and Scheme III' is an alternative for steps (d) and (e) as shown in Scheme I and Scheme I'.

A Mitsunobu reaction is a dehydration-condensation reaction between an alcohol and a nucleophilic reagent in the presence of an azo reagent and a phosphorus-containing reagent. The Mitsunobu process was reviewed by Hughes, Org. Reac. 1992, 42, 335.

In particular embodiments, the Mitsunobu reaction is performed in a solvent selected from 2-methyl tetrahydrofuran, dichloromethane, toluene, tetrahydrofuran, dioxane, tert-butyl methyl ether, acetonitrile, propionitrile, N,N-dimethylformamide, and N,N-dimethyl-2-imidazolidinone. In further embodiments, the Mitsunobu reaction is performed in a solvent selected from 2-methyl tetrahydrofuran, tetrahydrofuran, dichloromethane, toluene and acetonitrile. Examples of the phosphorus-containing reagent include triphenylphosphine, tri(o-tolyl)phosphine, tri(p-fluorophenyl)phosphine, tris(2,4,6-trimethoxyphenyl)phosphine, trimethylphosphine, and tri(n-butyl)phosphine, with triphenylphosphine being particularly preferred.

Examples of the azo reagent include diethyl azodicarboxylate (DEAD), diisopropyl azodicarboxylate (DIAD), di-tert-butyl azodicarboxylate (DBAD), tetramethylazodicarboxamide (TMAD), tetraisopropylazodicarboxamide (TIPA), azodicarbonyldipiperidine (ADDP), and dimethylhexahydrotetrazocinedione (DHTD). Of these, diethyl azodicarboxylate, diisopropyl azodicarboxylate, di-tert-butyl azodicarboxylate, and tetramethylazodicarboxamide are preferred, with diisopropyl azodicarboxylate and di-tert-butyl azodicarboxylate are particularly preferred.

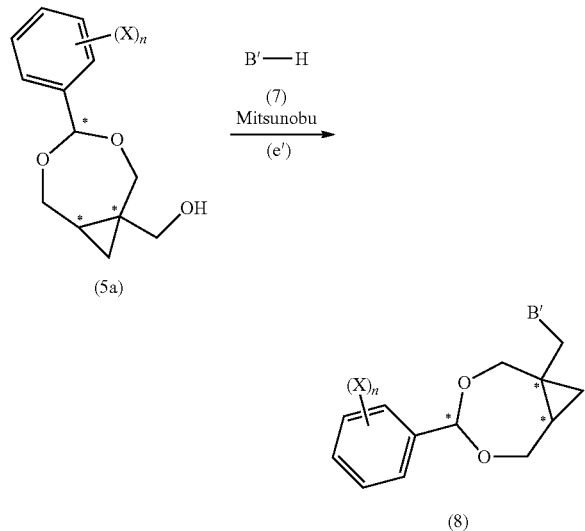

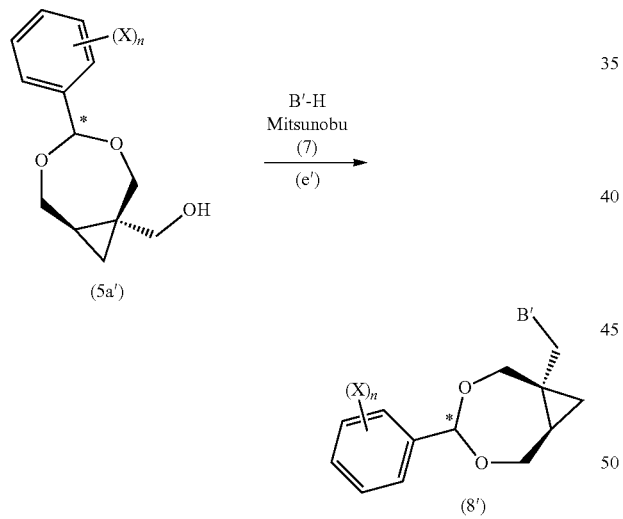

In certain embodiments, compounds of formula (8) or (8') can be obtained via the condensation of compounds of formula (5) or (5') with compounds of formula (7). Preferably, this is performed in the presence of triphenylphosphine and with a dialkylazodicarboxylate (DEAD) or di-p-chlorobenzyl azodicarboxylate, preferably in an aprotic solvent, such as THF and/or dichloromethane.

The compound of formula (A) or (A') may be obtained by hydrolysis of compounds of formula (8) or (8') in presence of an acid such as $TiCl_4$, $SnCl_4$, Ceric ammonium nitrate (CAN), $AlCl_3$, $HX^1$ with $X^1$ being halogen such as Cl, $H_2SO_4$, p-toluenesulfonic acid (pTSA) and the like. The hydrolysis can be performed in a solvent, such as a protic solvent, non-limiting examples of which include water and/or ethanol.

As shown in Scheme I and Scheme I', the substituent B' may be transformed to B during the hydrolysis or hydrogenation of the compounds of formula (8) or (8'). In particular embodiments, the substituent B' may be transformed further after hydrolysis or hydrogenation of the compounds of formula (8) or (8'), thereby obtaining the compound of formula (A) of (A').

In particular embodiments, the compound of formula (A) or (A') may be obtained by hydrogenation of compounds of formula (8) or (8'). As explained hereinabove, the hydrogenation reaction may be used for transforming the substituent B' to B. For example, B' may comprise nitro groups, which can be transformed to amino groups via hydrogenation. The hydrogenation reaction may also lead to the formation of the deprotected diol, especially in the presence of a metal, e.g. Pd or Ni, acting as a Lewis acid.

Compound (A) can be optionally purified. A non-limiting example of a suitable purification method is disclosed in EP0890574, which is hereby incorporated by reference.

Thus, the present invention also encompasses a method for the synthesis of cyclopropane derivatives of formula (A), (A') or (A"), which has a high stereoselectivity, has few reaction steps, involves an intermediate which is easy to purify, for example by crystallization. Furthermore, the method also provides high yields.

As indicated hereinabove, substituent $R^{11}$ in the compound of formula (5) is hydroxyl or amino. In particular embodiments, $R^{11}$ is amino. In a further embodiment, the method for the preparation of a compound of formula (A) or (A') can be performed as shown in Scheme IV or Scheme IV'.

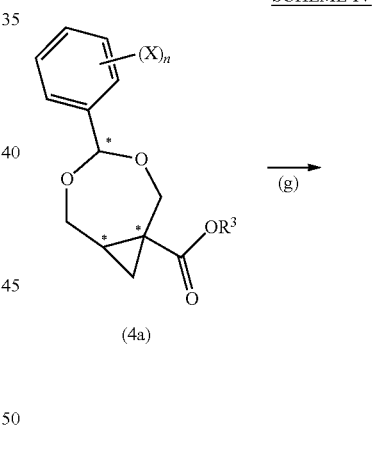

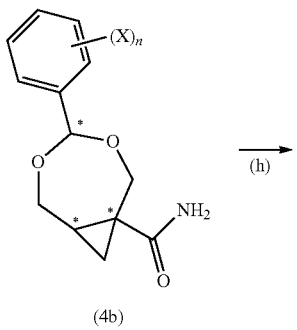

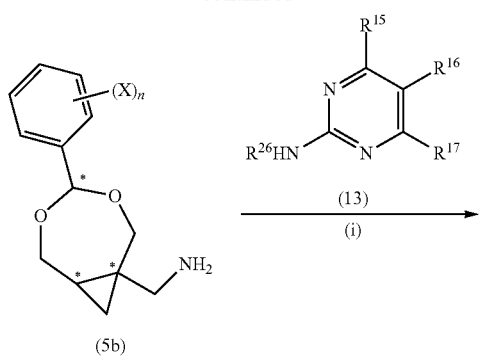

(5b)

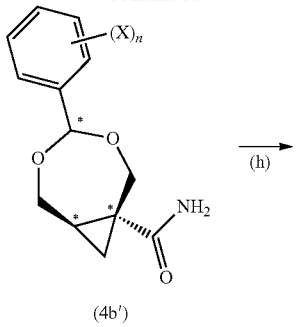

(4b')

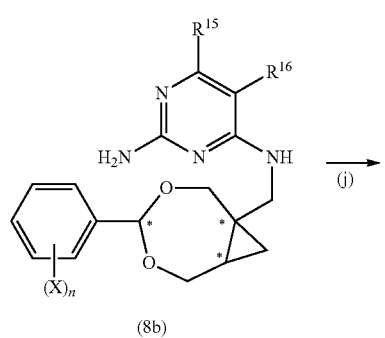

(8b)

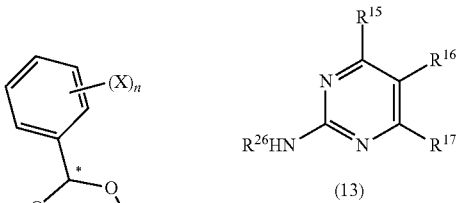

(5b')

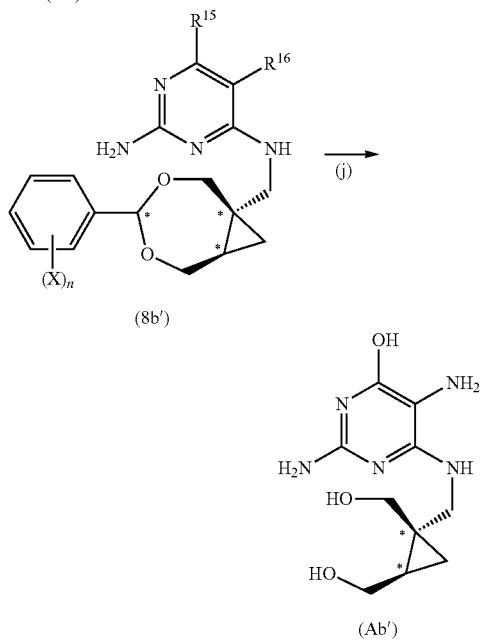

(8b')

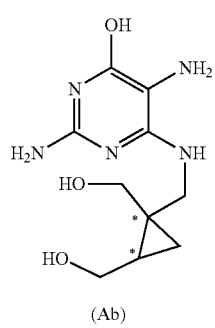

(Ab)

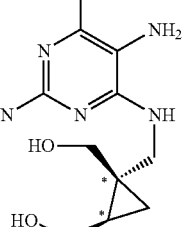

(Ab')

SCHEME IV'

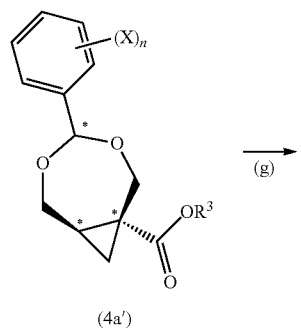

(4a')

In schemes IV and IV', $R^3$ is selected from $C_{1-6}$alkyl, $C_{6-10}$aryl, $C_{6-10}$aryl$C_{1-6}$alkylene, $C_{6-10}$haloaryl, $C_{1-6}$haloalkyl or $C_{6-10}$haloaryl$C_{1-6}$alkylene.

$R^{15}$ is $-OR^{27}$ or $R^{28}$. $R^{27}$ is selected from the group consisting of hydrogen, $C_{1-6}$alkyl, $C_{6-10}$aryl and $C_{6-10}$aryl$C_{1-6}$alkylene. $R^{28}$ is a leaving group, for example selected from halo, $C_{1-6}$alkoxy, $C_{1-6}$aryloxy, $C_{6-10}$aryl$C_{1-6}$alkyleneoxy, $C_{1-6}$alkylsulfinyl, $C_{6-10}$arylsulfinyl, $C_{6-10}$aryl$C_{1-6}$alkylenesulfinyl, $C_{1-6}$alkylsulfonyl, $C_{6-10}$arylsulfinyl, $C_{6-10}$aryl$C_{1-6}$alkylenesulfonyl, $C_{1-6}$alkylthio, $C_{6-10}$arylthio, $C_{6-10}$aryl$C_{1-6}$alkylenethio, $C_{1-6}$alkylsulfonate, $C_{6-10}$arylsulfonate, halo$C_{1-4}$ alkylsulfonate, $C_{1-6}$alkylphosphonate and $C_{6-10}$arylphosphonate. In particular embodiments, $R^{15}$ is $-OR^{27}$.

$R^{16}$ is selected from the group consisting of amino, nitro, formamido and hydrogen and $R^{17}$ is a leaving group. In particular embodiments, $R^{17}$ is selected from halo, $C_{1-6}$alkoxy, $C_{1-6}$aryloxy, $C_{6-10}$aryl$C_{1-6}$alkyleneoxy, $C_{1-6}$alkylsulfinyl, $C_{6-10}$arylsulfinyl, $C_{6-10}$aryl$C_{1-6}$alkylenesulfinyl, $C_{1-6}$alkylsulfonyl, $C_{6-10}$arylsulfinyl, $C_{6-10}$aryl$C_{1-6}$alkylenesulfonyl, $C_{1-6}$alkylthio, $C_{6-10}$arylthio, $C_{6-10}$aryl$C_{1-6}$alkylenethio, $C_{1-6}$alkylsulfonate, $C_{6-10}$arylsulfonate, halo$C_{1-4}$alkylsulfonate, $C_{1-6}$alkylphosphonate and $C_{6-10}$arylphosphonate. In certain embodiments, $R^{17}$ is selected from halo, $C_{1-6}$alkoxy, $C_{1-6}$aryloxy, $C_{6-10}$aryl$C_{1-6}$alkyleneoxy, $C_{1-6}$alkylsulfinyl, $C_{6-10}$arylsulfinyl, $C_{6-10}$aryl$C_{1-6}$alkylenesulfinyl, $C_{1-6}$alkylsulfonyl, $C_{6-10}$arylsulfinyl, $C_{6-10}$aryl$C_{1-6}$alkylenesulfonyl, $C_{1-6}$alkylthio, $C_{6-10}$arylthio, $C_{6-10}$aryl$C_{1-6}$alkylenethio, $C_{1-6}$alkylsulfonate, $C_{6-10}$arylsulfonate and halo$C_{1-4}$alkylsulfonate.

In particular embodiments, $R^{15}$ and $R^{17}$ are identical.

$R^{26}$ is hydrogen or an amino protecting group. In particular embodiments $R^{26}$ is selected from, hydrogen, $C_{6-10}$aryl$C_{1-6}$alkylene or $COR^{3o}$, $R^{3o}$ is selected from $C_{1-6}$alkyl, halo$C_{1-6}$alkyl, $C_{1-6}$alkyloxy, 9-fluorenylmethyloxy, or $C_{6-10}$aryl$C_{1-6}$alkyloxy. In certain embodiments, $R^{26}$ is selected from 9-fluroenylmethyloxycarbonyl, tert-butyloxycarbonyl, benzyloxycarbonyl, methylcarbonyl, benzyl and triphenylmethyl. In particular embodiments, $R^{26}$ is hydrogen.

In particular embodiments as illustrated in step (g) of schemes IV and IV', the method according to the present invention comprises the step of transforming the $COOR^3$ moiety of compound (4a) or (4a') into an amide moiety, thereby obtaining a compound (4b) or (4b'). The compound (4a) or (4a') can be obtained as described hereinabove. In certain embodiments, compounds (4a) or (4a') can be reacted with a source of ammonia, thereby obtaining compounds of formula (4b) or (4b'). In further embodiments, the ammonia source is ammonia in solution, an ammonium salt (e.g. ammonium chloride) or hexamethyldisilazane (HMDS). The reaction may be performed in a polar solvent such as water, methanol or ethanol.

In certain embodiments, the ester moiety ($COOR^3$) of compounds (4a) or (4a') can be hydrolyzed to a carboxyl group (COOH), which is then transformed to acid chloride (COCl) with a chlorinating agent such as thionyl chloride or oxalyl chloride. These reactions can be performed in a non protic solvent such as dichloromethane, acetonitrile or THF. The generated acid chloride can be reacted further with ammonia to produce compounds of formula (4b) or (4b').

In certain embodiments, the ester moiety of compounds (4a) or (4a') can be hydrolyzed to the corresponding acid and then reacted with ammonia in the presence of a coupling agent such as hydroxybenzotriazole (HOBt), benzotriazol-1-yl-oxytripyrrolidinophosphonium hexafluorophosphate (PyBOP) or 2-(1H-7-Azabenzotriazol-1-yl)-1,1,3,3-tetramethyl uronium hexafluorophosphate methanaminium (HATU) in a polar solvent such as dichloromethane or dimethylformamide (DMF).

In further embodiments, the amide moiety of compound (4b) or (4b') is reduced to an amine moiety, thereby obtaining a compound (5b) or (5b'), as illustrated in step (h) of schemes IV and IV'. The reduction may be obtained with one or more reducing agents such as borane complexes, for example $BH_3$-THF, or metal hydrides, for example $LiAlH_4$, $NaBH_4$, sodium triacetoxyborohydride ($NaBH(OAc)_3$) and $ZnBH_4$. In particular embodiments, the one or more reducing agents comprise an alkaline borohydride or an alkaline aluminium hydride, preferably $NaBH_4$ or $LiAlH_4$. Non-limiting examples of suitable solvents for the reduction reaction are ethanol or THF.

In particular embodiments, the compound (5b) or (5b') may be purified and/or isolated by crystallization, in a similar way as described herein for compound (5a) or (5a').

In certain embodiments, the compound (5b) or (5b') is reacted with a compound of formula (13), thereby obtaining a compound (8b) or (8b'), as illustrated in step (i) of schemes IV and IV'. The reaction may be carried out without or with a base such as N,N-diisopropylamine, potassium carbonate or cesium carbonate. In particular embodiments, the reaction may be performed in an aprotic solvent such as THF, DMF or N-Methylpyrrolidone (NMP). When $R^{26}$ is not hydrogen, the coupling with compound (13) can be followed by a deprotection step to afford a compound of formula (8b) or (8b').

In particular embodiments, more particularly when $R^{15}$ is $OR^{27}$, the compound (8b) or (8b') is hydrogenated, thereby obtaining a compound (Ab) or (Ab'), as illustrated in step (j) of schemes IV and IV'. The hydrogenation reaction results in the removal of the diol protecting group. When $R^{16}$ is nitro, the hydrogenation reaction will transform $R^{16}$ in amino.

In particular embodiments, $R^{16}$ is hydrogen, as represented by compound (8d) in Scheme V. Then, the amino group may be installed at position $R^{16}$ as shown in step (j') in Scheme V. This may be obtained by first reacting the compound (8d) with $NaNO_2$ and acetic acid, followed by reaction with $Na_2S_2O_4$ or $(NH_4)_2S$. Alternatively, the amino group may be installed at position $R^{16}$ by first reacting the compound (8d) with a p-chlorophenyldiazonium compound and acetic acid, followed by reduction, for example using $Zn/HCl/H_2O$. These reactions also result in the removal of the diol protecting group, resulting in a compound (8e).

In particular embodiments, more particularly when $R^{15}$ is $OR^{27}$, the installation of the amino group may be followed by a hydrogenation reaction as shown in step (j'') in Scheme V, thereby obtaining a compound (Ab).

SCHEME V

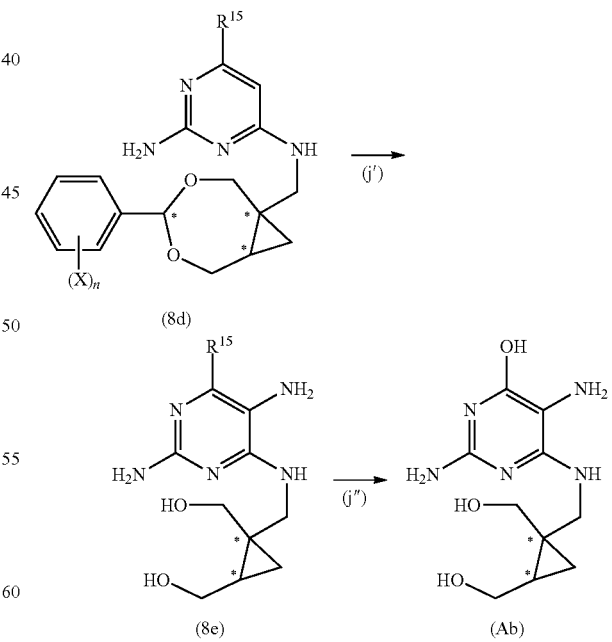

In particular embodiments, the compound (Ab) or (Ab') is further reacted with triethoxymethane or trimethoxymethane, thereby forming 2-amino-9-[[1,2-bis(hydroxymethyl)cyclopropyl]methyl]-1,9-dihydro-6H-purin-6-one (Ac), as shown in Scheme VI, or 2-amino-9-[[(1S,2R)-1,2-bis(hydroxymethyl)cyclopropyl]methyl]-1,9-dihydro-6H-purin-6-one (Ac'). In certain embodiments, HCl is used as a catalyst.

SCHEME VI

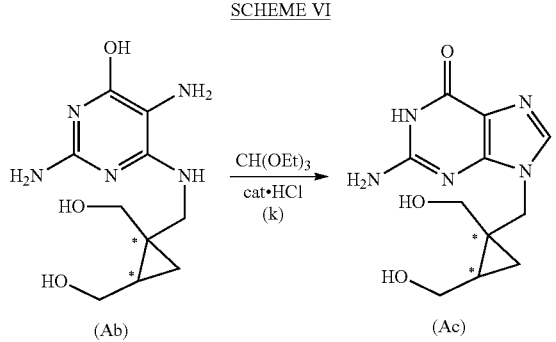 [SMILES: Nc1nc(O)c(N)c(NCC2(CO)CC2CO)n1 ; Nc1nc2c(ncn2CC2(CO)CC2CO)c(=O)[nH]1 ; "CH(OEt)3" ; "(Ac)"]

In a further aspect, the present invention provides a method for the preparation of a compound of formula (A)

(A)

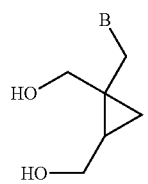

or a tautomer, a racemate, a stereoisomer, a pharmaceutically acceptable salt, a hydrate, or solvate thereof, wherein B is selected from the group consisting of purinyl, pyrimidyl, or aza or deaza analog thereof, or —$NR^1R^2$; each group being optionally substituted by one or more substituents independently selected from halo, amino, hydroxyl, $C_{1-6}$alkyl, amino$C_{1-6}$alkyl, nitro, formamido, —$NHR^{18}$, or $OR^7$; and wherein a carbon atom of said purinyl or pyrimidyl can be oxidized to form a C=O, wherein $R^7$ is selected from $C_{1-4}$alkyl, $C_{6-10}$aryl$C_{1-6}$alkylene or $C_{6-10}$aryl, $R^{18}$ is selected from $C_{6-10}$aryl$C_{1-6}$alkylene, $C_{1-6}$alkylcarbonyl, halo$C_{1-6}$alkylcarbonyl, $C_{1-6}$alkyloxycarbonyl, 9-fluorenylmethyloxycarbonyl, or $C_{6-10}$aryl$C_{1-6}$alkyloxycarbonyl; and $R^1$ is selected from hydrogen, $C_{6-10}$aryl, $C_{6-10}$aryl$C_{1-6}$alkylene, $C_{1-4}$alkyl, $C_{6-10}$haloaryl, $C_{1-4}$haloalkyl or $C_{6-10}$haloaryl$C_{1-6}$alkylene;

$R^2$ is selected from $C_{6-10}$aryl, $C_{6-10}$aryl$C_{1-6}$alkylene, $C_{1-4}$alkyl, $C_{6-10}$haloaryl, $C_{1-4}$haloalkyl or $C_{6-10}$haloaryl$C_{1-6}$alkylene;

comprising the step of coupling a compound of formula (10) or (12), (10)

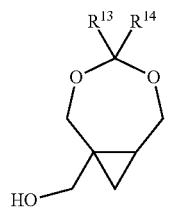

(12)

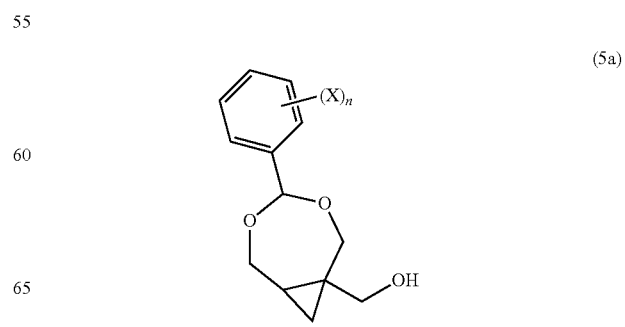

with a compound of formula B'—H under Mitsunobu conditions, wherein H is hydrogen, B' is B or selected from the group consisting of purinyl, pyrimidyl, or aza or deaza analog thereof, or —$NR^1R^2$; each group being optionally substituted by one or more substituents independently selected from halo, amino, hydroxyl, $C_{1-6}$alkyl, amino$C_{1-6}$alkyl, nitro, formamido, —$NHR^{18}$, or $OR^7$; and wherein a carbon atom of said purinyl or pyrimidyl can be oxidized to form a C=O, wherein $R^7$ is selected from $C_{1-4}$alkyl, $C_{6-10}$aryl$C_{1-6}$alkylene or $C_{6-10}$aryl, $R^{18}$ is selected from $C_{6-10}$aryl$C_{1-6}$alkylene, $C_{1-6}$alkylcarbonyl, halo$C_{1-6}$alkylcarbonyl, $C_{1-6}$alkyloxycarbonyl, 9-fluorenylmethyloxycarbonyl, or $C_{6-10}$aryl$C_{1-6}$alkyloxycarbonyl; and $R^1$ is selected from hydrogen, $C_{6-10}$aryl, $C_{6-10}$aryl$C_{1-6}$alkylene, $C_{1-4}$alkyl, $C_{6-10}$haloaryl, $C_{1-4}$haloalkyl or $C_{6-10}$haloaryl$C_{1-6}$alkylene;

$R^2$ is selected from $C_{6-10}$aryl, $C_{6-10}$aryl$C_{1-6}$alkylene, $C_{1-4}$alkyl, $C_{6-10}$haloaryl, $C_{1-4}$haloalkyl or $C_{6-10}$haloaryl$C_{1-6}$alkylene;

$R^{13}$ is selected from the group consisting of hydrogen, $C_{1-6}$alkyl, $C_{6-10}$aryl, $C_{6-10}$aryl$C_{1-6}$alkylene, $C_{6-10}$haloaryl, $C_{1-6}$haloalkyl, $C_{6-10}$haloaryl$C_{1-6}$alkylene, $C_{6-10}$aminoaryl, $C_{1-6}$aminoalkyl, $C_{6-10}$aminoaryl$C_{1-6}$alkylene and $C_{1-6}$alkoxy, and $R^{14}$ is a group selected from $C_{1-6}$alkyl, $C_{6-10}$aryl, $C_{6-10}$aryl$C_{1-6}$alkylene, $C_{6-10}$haloaryl, $C_{1-6}$haloalkyl, $C_{6-10}$haloaryl$C_{1-6}$alkylene, $C_{6-10}$aminoaryl, $C_{1-6}$aminoalkyl, $C_{6-10}$aminoaryl$C_{1-6}$alkylene and $C_{1-6}$alkoxy, each group being optionally substituted with one or more substituents each independently selected from $C_{1-6}$alkyl, $C_{1-6}$haloalkyl, $C_{2-6}$alkenyl, $C_{2-6}$alkynyl, halogen, hydroxyl, $C_{1-6}$alkoxy or amino.

In methods for the preparation of a compound of formula (A) known in the art, racemization can occur during the coupling of the compound of formula B'—H under certain conditions. The reaction under Mitsunobu conditions has the advantage of eliminating the risk of racemization. The resulting products can then be used in the preparation of a compound of formula (A), via a procedure as described hereinabove, for example the procedure according to Scheme I.

In further embodiments, the compound (10) is a compound of formula (5a) or (14)

(5a)

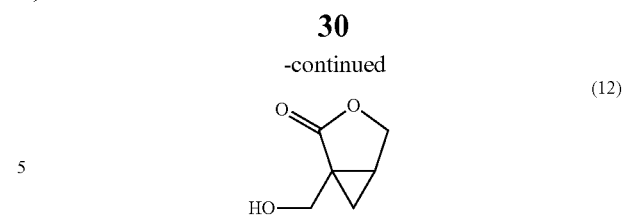

-continued

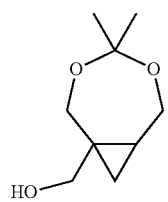

(14)

wherein n is an integer from 0 to 5, X is selected from $C_{1-6}$alkyl, $C_{1-6}$haloalkyl, $C_{2-6}$alkenyl, $C_{2-6}$alkynyl, halogen, hydroxyl, $C_{1-6}$alkoxy or amino.

The following examples illustrate the present invention.

EXAMPLES

The following examples are provided for the purpose of illustrating the present invention and by no means are meant and in no way should be interpreted to limit the scope of the present invention.

1) Preparation of ethyl (1R,2R)-1,2-bis(hydroxymethyl)cyclopropanecarboxylate (2c)

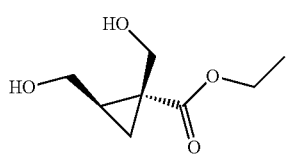

(2c)

In a reactor, ethanol (82.4 L) followed by ethyl (1S,5R)-2-oxo-3-oxabicyclo[3.1.0]hexane-1-carboxylate (10.3 kg, 64.6 mol) were added and cooled to 10° C. Sodium borohydride (1.85 kg, 51.7 mol) was added in lots over a period of 1 hour by maintaining the reaction temperature between 10-15° C. The reaction temperature was raised to 20-25° C. and maintained for 1 hour. The progress of the reaction was monitored by HPLC. After completion of the reaction, the reaction mass was cooled to 0-5° C. The pH of the reaction mass was adjusted to 7.0 using 1.5 N aqueous HCl at 0-5° C. during 1 hour. Ethyl acetate (34.0 L) was added to the reaction mass and the solid was filtered. The clear filtrate was distilled under reduced pressure at 40-45° C. to remove most of the solvent and the concentrate was dissolved in dichloromethane (103.0 L). The dichloromethane layer was washed with water (2×10.5 L). The aqueous layer was re-extracted with dichloromethane (3×10.5 L). The dichloromethane layers were combined and washed with brine (1×15.0 L). The organic layer was collected and distilled to remove most of the solvent at 40-45° C. under reduced pressure. The concentrate was passed over silica gel 60-120 mesh plug column using petroleum ether followed by 100% ethyl acetate as eluent to afford 5.0 kg (47.4%) of the title compound (2c).

2) Preparation of ethyl (1R,7R)-4-phenyl-3,5-dioxabicyclo[5.1.0]octane-1-carboxylate (4c)

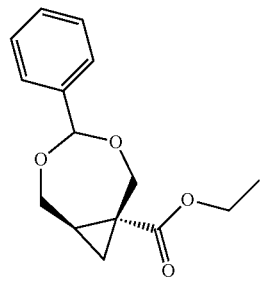

(4c)

A solution of ethyl (1R,2R)-1,2-bis(hydroxymethyl)cyclopropanecarboxylate (10.5 kg, 60.3 mol) in cyclohexane (105.0 L) was added in a reactor. Then, benzaldehyde dimethylacetal (11.6 kg, 76.4 mol) followed by camphor sulfonic acid (73.0 g) was added into the reactor. The reaction mass was heated to reflux and a portion of solvent was distilled azeotropically. The progress of the reaction was monitored by HPLC. On completion of the reaction, the reaction mass was distilled to remove most of the solvent under reduced pressure below 45° C. To the concentrate, petroleum ether (32.0 L) was added and stirred to precipitate the product. The slurry was cooled to 0-5° C. and stirred for 15 min. The slurry was filtered and washed with cold petroleum ether (11.0 L). The product was dissolved in dichloromethane (210.0 L) and washed with water (52.0 L) followed by brine (53.0 L). The organic layer was dried over sodium sulfate (5.5 kg) and was distilled to remove most of the solvent. Petroleum ether (21.0 L) was added and stirred at 25-30° C. for 30 min to get the complete precipitation of the product. The slurry was further cooled to 0-5° C. and stirred for 60 min. The slurry was filtered and washed with cold petroleum ether (11.0 L). The product was dried in a vacuum tray dryer for 12 hours below 45-50° C. to afford 10.25 Kg (64.5%) of the title compound (4c).

3) Preparation of [(1S,7R)-4-phenyl-3,5-dioxabicyclo[5.1.0]octan-1-yl]methanol (5c)

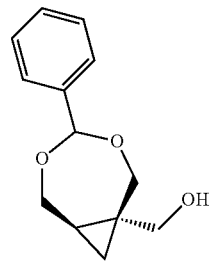

(5c)

Reaction.

In a reactor, tetrahydrofuran (110.0 L) was charged under nitrogen, followed by addition of ethyl (1R,7R)-4-phenyl-3,5-dioxabicyclo[5.1.0]octane-1-carboxylate (11.0 kg, 41.9 mol). The mixture was stirred to get a clear solution and cooled to 10-15° C. Lithium aluminium hydride (2 M in tetrahydrofuran, 17.1 L, 35.6 mol) was added drop wise over a period of 1 hour by maintaining the temperature at 10-15° C. The progress of the reaction was monitored by HPLC. After completion of the reaction, the reaction mass was cooled to 0-5° C. and quenched with subsequent addition of ethyl acetate (55.0 L) and brine (55.0 L) maintaining that temperature. The temperature of the reaction mass was gradually raised to 20-25° C. and stirred for 1 h. The organic layer was separated and washed with water (55.0 L) and brine (55.0 L). The organic layer was dried over sodium sulfate (6.0 kg) and the solvent was distilled off. Petroleum ether (22.0 L) was added to the residue to precipitate the product and the slurry was cooled to 0-5° C. and stirred for 30 min. The slurry was filtered and washed with cold petroleum ether (5.0 L). The product was dried in a vacuum tray dryer for 4 hours below 40-45° C. to afford 7.6 Kg of the title compound (5c) as crude product.

Purification.

In a reactor, ethyl acetate (27.5 L) was added followed by [(1S,7R)-4-phenyl-3,5-dioxabicyclo[5.1.0]octan-1-yl]methanol crude product (7.6 Kg) and the suspension was stirred to get a clear solution. The solution was heated to 65° C. for the complete dissolution. The solution was gradually cooled to 20-25° C. and the product started crystallizing from the solution. Petroleum ether (79.0 L) was added to the suspension and stirred. The resulting solution was cooled to 0-5° C. and the slurry was maintained at this temperature for 1 hour. The slurry was filtered and the product was washed with chilled petroleum ether (8.0 L). The product was dried in a vacuum tray dryer for 12 hours below 40-45° C. to afford 6.1 Kg (66.2%) of the title compound (5c).

4) Preparation of [(1R,7R)-4-phenyl-3,5-dioxabicyclo[5.1.0]octan-1-yl]methyl methanesulfonate (6c)

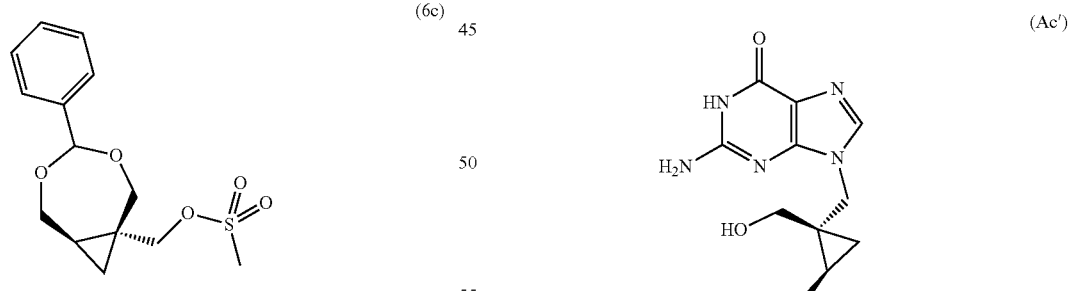

(6c)

In a reactor, a solution of mesyl chloride (280 g, 2.4 mol) in dichloromethane (2 L) was added to a mixture of [(1S,7R)-4-phenyl-3,5-dioxabicyclo[5.1.0]octan-1-yl]methanol (450 g, 2.0 mol) and triethylamine (310 g, 3.1 mol) in dichloromethane (4.7 L). A maximum internal temperature of 27° C. was observed. The mixture was stirred for 1 hour. Water (4.5 L) was added, phases were separated and the aqueous phase was extracted with dichloromethane (2.3 L). The combined organic phases were washed with water (2.3 L) and subsequently concentrated under reduced pressure yielding off-white solid product. This material was used as such in the next reaction step without further purification.

5) Preparation of 6-chloro-9-(((1S,7R)-4-phenyl-3,5-dioxabicyclo[5.1.0]octan-1-yl)methyl)-9H-purin-2-amine (8c)

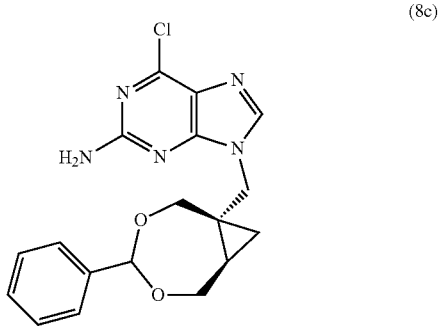

(8c)

In a reactor, chloropurine (specifically, 6-chloro-9H-purin-2-amine) (220 g, 1.3 mol) and potassium carbonate (800 g, 5.8 mol) were charged. Crude product of the previous step was dissolved in acetonitrile (16 L). A part of this solution (12.8 L) was added to the reactor with additional acetonitrile (1 L). The mixture was heated to reflux, and stirred at this temperature for 6 h. The mixture was allowed to cool and stirred at ambient temperature overnight. Reaction was complete. The solids were removed by filtration. The filtercake was washed twice with acetonitrile (0.75 L). The filtrate was concentrated under reduced pressure to a volume of ~2 L and was submitted as such to the next step.

6) Preparation of 2-amino-9-[[(1S,2R)-1,2-bis(hydroxymethyl)cyclopropyl]methyl]-1,9-dihydro-6H-purin-6-one (Ac′)

(Ac′)

Hydrochloric acid (1 N, 5 L) and extra acetonitrile (0.5 L) were added to the suspension (2 L) of the previous step. The reaction mixture was heated to reflux and distillate (~1.5 L) was removed. After 16 hours the reaction was stopped. The reaction mixture was extracted with methyl-tert-butylether (2×1 L). The resulting aqueous layer was set to pH=6.4 by the addition of sodium hydroxide (6 M, 1 L). The temperature increased to ~35° C. and a green solution was obtained. The batch was cooled and crystallization occurred at ~20° C. After 48 hours stirring the batch was cooled to 10° C. and filtered.

The crystalline mass was washed with chilled water (1 L). The wet product (436 g) was dried under reduced pressure at 40° C. for 36 hours, yielding 185 g of the title compound as crude product.

7) Purification of 2-amino-9-[[(1S,2R)-1,2-bis(hydroxymethyl)cyclopropyl]methyl]-1,9-dihydro-6H-purin-6-one (Ac') via its sodium salt Crude product of the previous step (185 g) was suspended in methanol (0.9 L). Sodium methoxide (0.26 L, 5.4 M in methanol) was added at 15° C. A darkly colored solution was obtained. The mixture was stirred for 0.5 hour at ambient temperature, and was subsequently cooled to 3° C. White crystalline material appeared in a greenish-gray liquid. The sodium salt was isolated by filtration, and washed with cold methanol (0.3 L). The wet cake (255 g) was dried under reduced pressure at 30-40° C., to afford 115 g sodium salt of the title compound. Sodium salt of the title compound (110 g) was suspended in water (550 ml) at ambient temperature. Aqueous hydrochloric acid (2 M, 170 ml) was added to the suspension. An exothermic temperature increase to $T_{in}=25°$ C. was observed and the pH of the mixture was 6.4. The slurry was stirred for 0.5 hour at ~25° C., and then, cooled to 4° C. The crystal slurry was filtered and washed with water (100 ml). The resulting grayish clay was dried under reduced pressure at 30-40° C. to afford 94 g of the title compound with high purity.

In particular embodiments, steps 4) and 5) as described hereinabove may be replaced by the coupling of compound (5c) with 6-chloro-9H-purin-2-amine under Mitsunobu conditions, thereby obtaining compound (8c). Compound (8c) can then be further reacted to obtain compound (Ac'). This is illustrated by the following non-limiting examples.

4') Preparation of 6-chloro-9-(((1S,7R)-4-phenyl-3,5-dioxabicyclo[5.1.0]octan-1-yl)methyl)-9H-purin-2-amine (8c) under Mitsunobu conditions

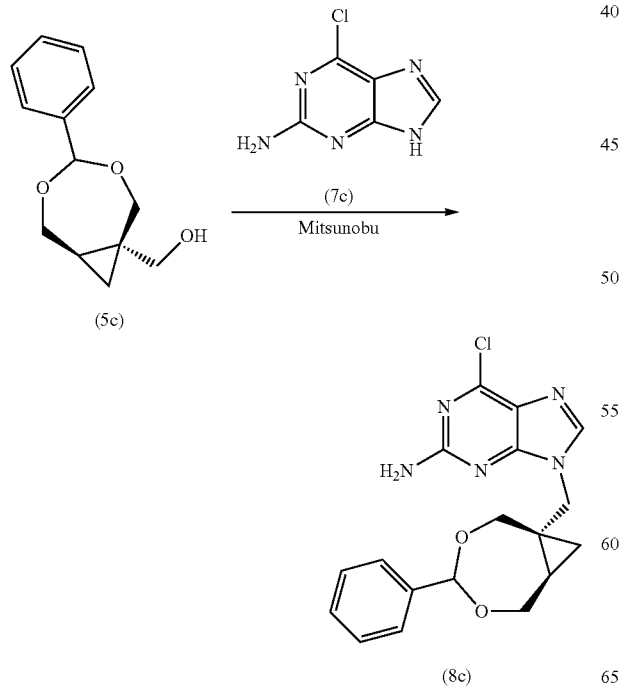

In a reactor, a mixture of [(1S,7R)-4-phenyl-3,5-dioxabicyclo[5.1.0]octan-1-yl]methanol (750 g, 3.4 mol) (5c), 6-chloro-9H-purin-2-amine (7c) (479 g, 2.8 mol) and triphenylphosphine (930 g, 3.5 mol) in 2-methyltetrahydrofuran (7.4 L) was stirred at room temperature for 30 minutes, and then heated to 65° C. (+/−5° C.). To this mixture was dosed a solution of DIAD (711 g, 3.5 mol) in 2-methyltetrahydrofuran (740 mL) over a period of 1 hour. The mixture was stirred during 1 hour at reflux and then allowed to cool to room temperature overnight. Solids were removed by filtration. The reactor was rinsed with 2-methyltetrahydrofuran (740 mL) and this liquid was used to wash the solids on the filter. The filtrate was submitted as such in the next step (6').

6') Preparation of 2-amino-9-[[(1S,2R)-1,2-bis(hydroxymethyl)cyclopropyl]methyl]-1,9-dihydro-6H-purin-6-one (Ac')

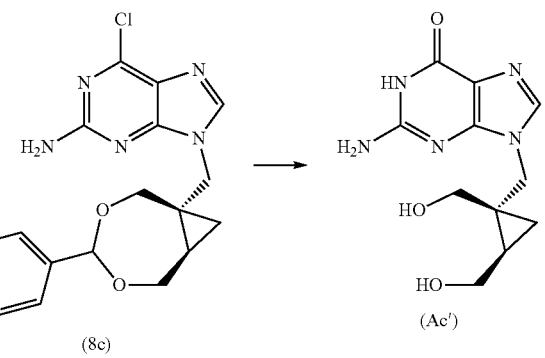

The filtrate of the previous step (4') was charged to a reactor. The recipient which contained the filtrate was rinsed with 2-methyltetrahydrofuran (740 mL), which was then added to the reactor. To this solution was added a solution of 2M aqueous hydrochloric acid. The reactor content was heated to 70° C. (+/−5° C.). After 2 hours the mixture was cooled to room temperature. The aqueous and organic phases were separated. Then, the aqueous phase was extracted with 2-methyltetrahydrofuran (2×3.7 L), followed by an extraction with tert-butyl methyl ether (3.8 L). The pH of the resulting aqueous phase was set to 6.5 (+/−0.5) by the addition of aqueous sodium hydroxide, while keeping the batch temperature below 40° C. The mixture was allowed to cool to room temperature and was stirred overnight. The crude product was isolated by filtration and washed with water (1.5 L). The isolated wet product was dried at 40 (+/−5° C. under reduced pressure, yielding 357 g of 2-amino-9-[[(1S,2R)-1,2-bis(hydroxymethyl)cyclopropyl]methyl]-1,9-dihydro-6H-purin-6-one (Ac') as crude product.

What is claimed is:
1. A compound of the formula (5):

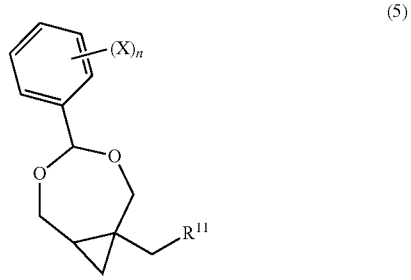

or a tautomer, racemate or stereoisomer thereof, wherein n is an integer from 0 to 5, X is selected from C$_{1-6}$alkyl, C$_{2-6}$alkenyl, C$_{2-6}$alkynyl, halogen, hydroxyl, C$_{1-6}$alkoxy or amino; and R$^{11}$ is hydroxyl or amino.

2. The compound according to claim 1, which is an compound of formula (5'):

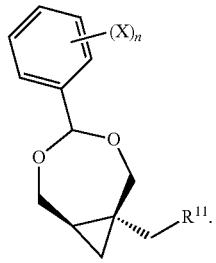

(5')

3. A method for the preparation of a compound of formula (5) or a tautomer, racemate or stereoisomer thereof, according to claim 1:

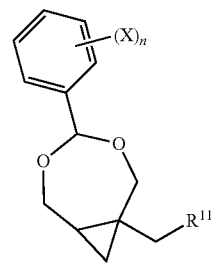

(5)

wherein n, X and R$^{11}$ have the same meaning as that defined in claim 1, comprising the step of transforming the —COR$^{12}$ moiety of a compound of formula (4) thereby obtaining the compound of formula (5);

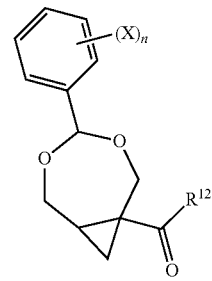

(4)

wherein R$^{12}$ is —OR$^3$ or amino and R$^3$ is selected from C$_{1-6}$alkyl, C$_{6-10}$aryl, C$_{6-10}$arylC$_{1-6}$alkylene, C$_{6-10}$haloaryl, C$_{1-6}$haloalkyl or C$_{6-10}$haloarylC$_{1-6}$alkylene.

4. The method according to claim 3, wherein the preparation of said compound of formula (4) comprises reacting a compound of formula (2) with a compound of formula (3):

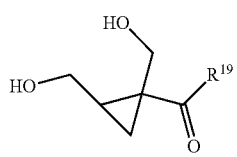

(2)

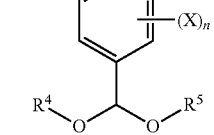

(3)

thereby obtaining a compound (4a)

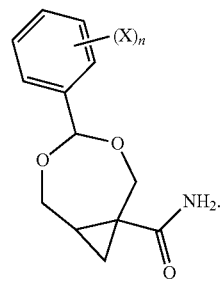

(4a)

wherein R$^{19}$ is OR$^{23}$ and R$^{23}$ is selected from C$_{1-6}$alkyl, C$_{6-10}$aryl, C$_{6-10}$arylC$_{1-6}$alkylene, C$_{6-10}$haloaryl, C$_{1-6}$haloalkyl or C$_{6-10}$haloarylC$_{1-6}$alkylene, and R$^4$ and R$^5$ are each independently selected from C$_{1-6}$alkyl, C$_{6-10}$arylC$_{1-6}$alkylene or C$_{6-10}$aryl.

5. The method according to claim 4, further comprising the step of transforming the ester moiety of compound (4a) into an amide moiety, thereby obtaining a compound of formula (4b),

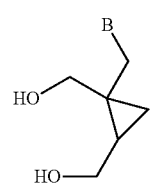

(4b)

6. A method for the production of a compound of formula (A):

(A)

or a tautomer, a racemate, a stereoisomer, a pharmaceutically acceptable salt, a hydrate, or solvate thereof, wherein B is selected from the group comprising purinyl, pyrimidyl, or aza or deaza analog thereof, or —NR$^1$R$^2$; each group being optionally substituted by one or more substituents independently selected from halo, amino, hydroxyl, C$_{1-6}$alkyl, aminoC$_{1-6}$alkyl, nitro, formamido, —NHR$^{18}$ or OR$^7$; and wherein a carbon atom of said purinyl or pyrimidyl can be oxidized to form a C═O, wherein R$^7$ is selected from C$_{1-4}$alkyl, C$_{6-10}$arylC$_{1-6}$alkylene or C$_{6-10}$aryl, R$^{18}$ is selected from C$_{6-10}$arylC$_{1-6}$alkylene, C$_{1-6}$alkylcarbonyl, haloC$_{1-6}$alkylcarbonyl, C$_{1-6}$alkyloxycarbonyl, 9-fluorenylmethyloxycarbonyl, or C$_{6-10}$arylC$_{1-6}$alkyloxycarbonyl; and R$^1$ is selected from hydrogen, C$_{6-10}$aryl, C$_{6-10}$arylC$_{1-6}$alkylene, C$_{6-10}$haloaryl, C$_{1-4}$haloalkyl or C$_{6-10}$haloarylC$_{1-6}$alkylene;

R$^2$ is selected from C$_{6-10}$aryl, C$_{6-10}$arylC$_{1-6}$alkylene, C$_{6-10}$haloaryl, C$_{1-4}$haloalkyl or C$_{6-10}$haloarylC$_{1-6}$alkylene;

comprising the step of hydrolyzing or reducing a compound of formula (8);

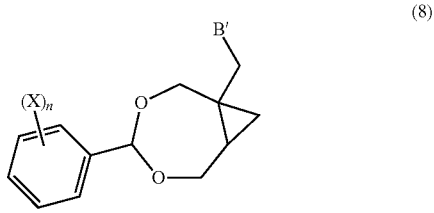

(8)

wherein n is an integer from 0 to 5 and X is C$_{1-6}$alkyl, C$_{1-6}$haloalkyl C$_{2-6}$alkenyl, C$_{2-6}$alkynyl, halogen, hydroxyl, C$_{1-6}$alkoxy or amino; and wherein B' is B or selected from the group consisting of purinyl, pyrimidyl, or aza or deaza analog thereof, or —NR$^1$R$^2$; each group being optionally substituted by one or more substituents independently selected from halo, amino, hydroxyl, C$_{1-6}$alkyl, aminoC$_{1-6}$alkyl, nitro, formamido, —NHR$^{18}$, —NR$^{24}$R$^{25}$ or OR$^7$; and wherein a carbon atom of said purinyl or pyrimidyl can be oxidized to form a C═O, wherein R$^7$ is selected from C$_{1-4}$alkyl, C$_{6-10}$arylC$_{1-6}$alkylene or C$_{6-10}$aryl, R$^{18}$ is selected from C$_{6-10}$arylC$_{1-6}$alkylene, C$_{1-6}$alkylcarbonyl, haloC$_{1-6}$alkylcarbonyl, C$_{1-6}$alkyloxycarbonyl, 9-fluorenylmethyloxycarbonyl, or C$_{6-10}$arylC$_{1-6}$alkyloxycarbonyl, R$^{24}$ and R$^{25}$ are independently hydrogen or C$_{1-6}$alkyl; and R$^1$ is selected from hydrogen, C$_{6-10}$aryl, C$_{6-10}$arylC$_{1-6}$alkylene, C$_{1-4}$alkyl, C$_{6-10}$haloaryl, C$_{1-4}$haloalkyl or C$_{6-10}$haloarylC$_{1-6}$alkylene;

R$^2$ is selected from C$_{6-10}$aryl, C$_{6-10}$arylC$_{1-6}$alkylene, C$_{1-4}$alkyl, C$_{6-10}$haloaryl, C$_{1-4}$haloalkyl or C$_{6-10}$haloarylC$_{1-6}$alkylene.

7. The method according to claim 6, wherein said compound of formula (8) is prepared by coupling a compound of formula (5a) with a compound of formula B'—H,

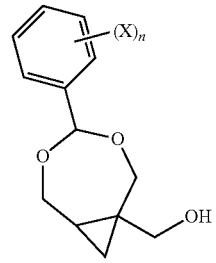

(5a)

wherein n is an integer from 0 to 5, X is selected from C$_{1-6}$alkyl, C$_{2-6}$alkenyl, C$_{2-6}$alkynyl, halogen, hydroxyl, C$_{1-6}$alkoxy or amino; and R$^{11}$ is hydroxyl or amino;

B' has the same meaning as that defined in claim 6; and

H is hydrogen.

8. The method according to claim 7, wherein prior to coupling compound of formula (5a) with compound B'—H, the hydroxyl moiety of the compound of formula (5) is transformed to obtain a compound of formula (6):

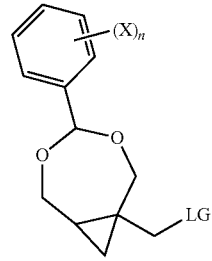

(6)

wherein LG represents a leaving group selected from halo, mesylate, tosylate, azide, nosylate, triflate, cyano or imidazolyl.

9. The method according to claim 6, wherein the preparation of said compound of formula (8) comprises reacting a compound of formula (5b) with a compound of formula (13),

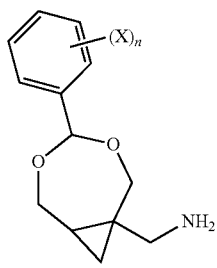

(5b)

-continued

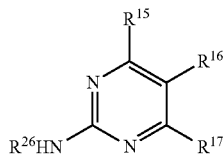
(13)

wherein $R^{15}$ is —$OR^{27}$ or $R^{28}$, $R^{16}$ is selected from the group consisting of amino, nitro, formamido and hydrogen, $R^{17}$ is selected from halo, $C_{1-6}$alkoxy, $C_{1-6}$aryloxy, $C_{6-10}$aryl$C_{1-6}$alkyleneoxy, $C_{1-6}$alkylsulfinyl, $C_{6-10}$arylsulfinyl, $C_{6-10}$aryl$C_{1-6}$alkylenesulfinyl, $C_{1-6}$alkylsulfonyl, $C_{6-10}$arylsulfinyl, $C_{6-10}$aryl$C_{1-6}$alkylenesulfonyl, $C_{1-6}$alkylthio, $C_{6-10}$arylthio, $C_{6-10}$aryl$C_{1-6}$alkylenethio, $C_{1-6}$alkylsulfonate, $C_{6-10}$arylsulfonate, halo$C_{1-4}$alkylsulfonate, $C_{1-6}$alkylphosphonate and $C_{6-10}$arylphosphonate;

$R^{27}$ is selected from the group consisting of hydrogen, $C_{1-6}$alkyl, $C_{6-10}$aryl and $C_{1-10}$aryl$C_{1-6}$alkylene, $R^{28}$ is selected from halo, $C_{1-6}$alkoxy, $C_{1-6}$aryloxy, $C_{6-10}$aryl$C_{1-6}$alkyleneoxy, $C_{1-6}$alkylsulfinyl, $C_{6-10}$arylsulfinyl, $C_{6-10}$aryl$C_{1-6}$alkylenesulfinyl, $C_{1-6}$alkylsulfonyl, $C_{6-10}$arylsulfinyl, $C_{6-10}$aryl$C_{1-6}$alkylenesulfonyl, $C_{1-6}$alkylthio, $C_{6-10}$arylthio, $C_{6-10}$aryl$C_{1-6}$alkylenethio, $C_{1-6}$alkylsulfonate, $C_{6-10}$arylsulfonate, halo$C_{1-4}$alkylsulfonate, $C_{1-6}$alkylphosphonate and $C_{6-10}$arylphosphonate; and $R^{26}$ is selected from, hydrogen, $C_{6-10}$aryl$C_{1-6}$alkylene or $COR^{30}$, wherein $R^{30}$ is selected from $C_{1-6}$alkyl, halo$C_{1-6}$alkyl, $C_{1-6}$alkyloxy, 9-fluorenylmethyloxy, or $C_{6-10}$aryl$C_{1-6}$alkyloxy.

10. The method according to claim 7, wherein compound (5a) is prepared using a method comprising the step of transforming the —$COR^{12}$ moiety of a compound of formula (4) thereby obtaining the compound of formula (5a),

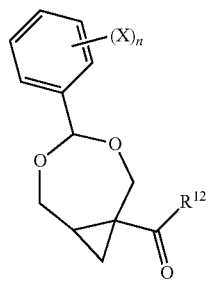
(4)

wherein $R^{12}$ is —$OR^3$ or amino and $R^3$ is selected from $C_{1-6}$alkyl, $C_{6-10}$aryl, $C_{6-10}$aryl$C_{1-6}$alkylene, $C_{6-10}$haloaryl, $C_{1-6}$haloalkyl or $C_{6-10}$haloaryl$C_{1-6}$alkylene.

11. The method according to claim 10, further comprising the step of crystallizing and purifying said compound of formula (5a) or (5b).

12. The method according to claim 6, wherein the compound of formula (A) is a compound of formula (A'):

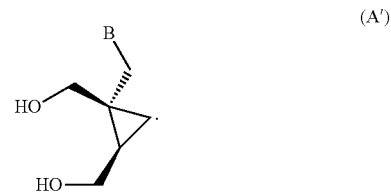
(A')

13. A method for the preparation of a compound of formula (A)

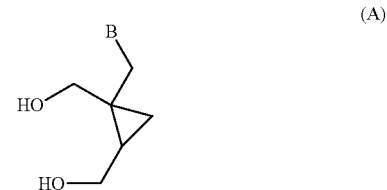
(A)

or a tautomer, a racemate, a stereoisomer, a pharmaceutically acceptable salt, a hydrate, or solvate thereof,
wherein B is selected from the group comprising purinyl, pyrimidyl, or aza or deaza analog thereof, or —$NR^1R^2$; each group being optionally substituted by one or more substituents independently selected from halo, amino, hydroxyl, $C_{1-6}$alkyl, amino$C_{1-6}$alkyl, nitro, formamido, —$NHR^{18}$ or $OR^7$; and wherein a carbon atom of said purinyl or pyrimidyl can be oxidized to form a C=O, wherein $R^7$ is selected from $C_{1-4}$alkyl, $C_{6-10}$aryl$C_{1-6}$alkylene or $C_{6-10}$aryl, $R^{18}$ is selected from $C_{6-10}$aryl$C_{1-6}$alkylene, $C_{1-6}$alkylcarbonyl, halo$C_{1-6}$alkylcarbonyl, $C_{1-6}$alkyloxycarbonyl, 9-fluorenylmethyloxycarbonyl, or $C_{6-10}$aryl$C_{1-6}$alkyloxycarbonyl; and $R^1$ is selected from hydrogen, $C_{6-10}$aryl, $C_{6-10}$aryl$C_{1-6}$alkylene, $C_{6-10}$haloaryl, $C_{1-4}$haloalkyl or $C_{6-10}$haloaryl$C_{1-6}$alkylene;

$R^2$ is selected from $C_{6-10}$aryl, $C_{6-10}$aryl$C_{1-6}$alkylene, $C_{6-10}$haloaryl, $C_{1-4}$haloalkyl or $C_{6-10}$haloaryl$C_{1-6}$alkylene;

comprising the step of coupling a compound of formula (10) or (12),

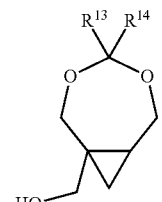
(10)

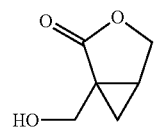
(12)

with a with a compound of formula B'—H under Mitsunobu conditions, wherein H is hydrogen, wherein B' is B or selected from the group consisting of purinyl, pyrimidyl, or aza or deaza analog thereof, or —NR$^1$R$^2$; each group being optionally substituted by one or more substituents independently selected from halo, amino, hydroxyl, $C_{1-6}$alkyl, amino$C_{1-6}$alkyl, nitro, formamido, —NHR$^{18}$, —NR$^{24}$R$^{25}$ or OR$^7$; and wherein a carbon atom of said purinyl or pyrimidyl can be oxidized to form a C=O, wherein R$^7$ is selected from $C_{1-4}$alkyl, $C_{6-10}$aryl$C_{1-6}$alkylene or $C_{6-10}$aryl, R$^{18}$ is selected from $C_{6-10}$aryl$C_{1-6}$alkylene, $C_{1-6}$alkylcarbonyl, halo$C_{1-6}$alkylcarbonyl, $C_{1-6}$alkyloxycarbonyl, 9-fluorenylmethyloxycarbonyl, or $C_{6-10}$aryl$C_{1-6}$alkyloxycarbonyl, R$^{24}$ and R$^{25}$ are independently hydrogen or $C_{1-6}$alkyl; and R$^1$ is selected from hydrogen, $C_{6-10}$aryl, $C_{6-10}$aryl$C_{1-6}$alkylene, $C_{1-4}$alkyl, $C_{6-10}$haloaryl, $C_{1-4}$haloalkyl or $C_{6-10}$haloaryl$C_{1-6}$alkylene;

R$^2$ is selected from $C_{6-10}$aryl, $C_{6-10}$aryl$C_{1-6}$alkylene, $C_{1-4}$alkyl, $C_{6-10}$haloaryl, $C_{1-4}$haloalkyl or $C_{6-10}$haloaryl$C_{1-6}$alkylene;

R$^{13}$ is selected from the group consisting of hydrogen, $C_{1-6}$alkyl, $C_{6-10}$aryl, $C_{6-10}$aryl$C_{1-6}$alkylene, $C_{6-10}$haloaryl, $C_{1-6}$haloalkyl, $C_{6-10}$haloaryl$C_{1-6}$alkylene, $C_{6-10}$aminoaryl, $C_{1-6}$aminoalkyl, $C_{6-10}$aminoaryl$C_{1-6}$alkylene and $C_{1-6}$alkoxy, and R$^{14}$ is a group selected from $C_{1-6}$alkyl, $C_{6-10}$aryl, $C_{6-10}$aryl$C_{1-6}$alkylene, $C_{6-10}$haloaryl $C_{1-6}$haloalkyl, $C_{6-10}$haloaryl$C_{1-6}$alkylene, $C_{6-10}$aminoaryl, $C_{1-6}$aminoalkyl, $C_{6-10}$aminoaryl$C_{1-6}$alkylene and $C_{1-6}$alkoxy, each group being optionally substituted with one or more substituents each independently selected from $C_{1-6}$alkyl, $C_{1-6}$haloalkyl, $C_{2-6}$alkenyl, $C_{2-6}$alkynyl, halogen, hydroxyl, $C_{1-6}$alkoxy or amino.

14. The method according to claim 13, wherein said compound of formula (10) is a compound of formula (5a) or (14)

(5a)

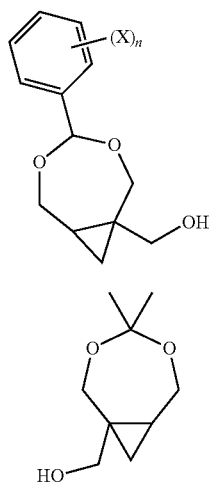

(14)

wherein n is an integer from 0 to 5, X is selected from $C_{1-6}$alkyl, $C_{1-6}$haloalkyl, $C_{2-6}$alkenyl, $C_{2-6}$alkynyl, halogen, hydroxyl, $C_{1-6}$alkoxy or amino.

15. The method according to claim 9, wherein compound (5b) is prepared using a method comprising the step of transforming the —COR$^{12}$ moiety of a compound of formula (4) thereby obtaining the compound of formula (5b);

(4)

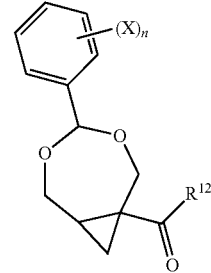

wherein R$^{12}$ is —OR$^3$ or amino and R$^3$ is selected from $C_{1-6}$alkyl, $C_{6-10}$aryl, $C_{6-10}$aryl$C_{1-6}$alkylene, $C_{6-10}$haloaryl, $C_{1-6}$haloalkyl or $C_{6-10}$haloaryl$C_{1-6}$alkylene.

16. The method according to claim 9, wherein compound (5b) is prepared using a method comprising reacting a compound of formula (2) with a compound of formula (3):

(2)

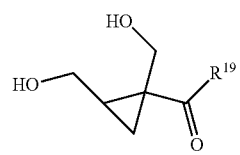

(3)

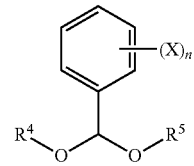

thereby obtaining a compound (4a)

(4a)

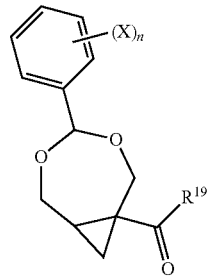

wherein R$^{19}$ is OR$^{23}$ and R$^{23}$ is selected from $C_{1-6}$alkyl, $C_{6-10}$aryl, $C_{6-10}$aryl$C_{1-6}$alkylene, $C_{6-10}$haloaryl, $C_{1-6}$haloalkyl or $C_{6-10}$haloaryl$C_{1-6}$alkylene, and R$^4$ and R$^5$ are each independently selected from $C_{1-6}$alkyl, $C_{6-10}$aryl$C_{1-6}$alkylene or $C_{6-10}$aryl;

followed by transforming the ester moiety of compound (4a) into an amide moiety, thereby obtaining a compound of formula (5b).

* * * * *